(12) United States Patent
Chan et al.

(10) Patent No.: US 8,584,299 B2
(45) Date of Patent: Nov. 19, 2013

(54) ELECTRIC TOOTHBRUSHES

(75) Inventors: John Geoffrey Chan, Maineville, OH (US); Douglas A. Gall, Strongsville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 849 days.

(21) Appl. No.: 11/880,907

(22) Filed: Jul. 25, 2007

(65) Prior Publication Data

US 2011/0185520 A9 Aug. 4, 2011

Related U.S. Application Data (63) Continuation of application No. 10/825,792, filed on Apr. 16, 2004, now abandoned.

(60) Provisional application No. 60/464,787, filed on Apr. 23, 2003.

(51) Int. Cl.
*A46B 9/04* (2006.01)
*A61C 17/22* (2006.01)

(52) U.S. Cl.
USPC ............. 15/110; 15/22.1; 15/22.2; 15/28; 601/142

(58) Field of Classification Search
USPC .......................................................... 15/110
IPC ....................................................... A46B 9/04
See application file for complete search history.

(56) References Cited

U.S. PATENT DOCUMENTS

| 90,763 | A | 6/1869 | Marshall |
|---|---|---|---|
| 301,644 | A | 7/1884 | Thompson |
| 585,358 | A | 6/1897 | Gould |
| 669,402 | A | 3/1901 | Rose |
| 759,490 | A | 5/1904 | Yates |
| 864,054 | A | 8/1907 | Abrams |
| 876,317 | A | 1/1908 | Booth |
| 914,501 | A | 3/1909 | McEachern |
| 1,018,927 | A | 2/1912 | Sarrazin |
| 1,022,920 | A | 4/1912 | Anderson |
| 1,125,532 | A | 1/1915 | Himmel |

(Continued)

FOREIGN PATENT DOCUMENTS

| CH | 99738 | 6/1923 |
|---|---|---|
| CH | 460705 | 10/1968 |

(Continued)

OTHER PUBLICATIONS

PCT International Search Report dated Feb. 15, 2005.

(Continued)

*Primary Examiner* — Monica Carter
*Assistant Examiner* — Stephanie Berry
(74) *Attorney, Agent, or Firm* — John P. Colbert; George H. Leal (57) ABSTRACT

A toothbrush has a body, a brush head, and a neck extending between the body and the brush head. The toothbrush also has a massaging element, a plurality of bristles, and a plurality of massaging tips. The brush head has a front face and a rear face. The massaging element is disposed on the rear face of the brush head, while the plurality of bristles and the plurality of massaging tips extend from the front face.

21 Claims, 5 Drawing Sheets

(56) References Cited

U.S. PATENT DOCUMENTS

| | | |
|---|---|---|
| 1,128,139 A | 2/1915 | Hoffman |
| 1,191,556 A | 7/1916 | Blake |
| 1,251,250 A | 12/1917 | Libby |
| 1,268,544 A | 6/1918 | Cates |
| 1,337,173 A | 4/1920 | White |
| 1,327,757 A | 11/1920 | Eggers |
| 1,691,863 A | 11/1920 | Van Sant |
| 1,405,279 A | 1/1922 | Cassedy |
| 1,440,785 A | 1/1923 | Levis |
| 1,456,535 A | 5/1923 | Cartwright |
| 1,466,723 A | 9/1923 | Izawa |
| 1,476,519 A | 12/1923 | Karl |
| 1,494,448 A | 5/1924 | Joseph |
| 1,495,675 A | 5/1924 | Colt |
| 1,526,267 A | 2/1925 | Dessau |
| 1,578,074 A | 3/1926 | Chandler |
| 1,588,785 A | 6/1926 | Van Sant |
| 1,598,224 A | 8/1926 | Van Sant |
| 1,624,054 A | 4/1927 | Kuhne |
| 1,642,465 A | 9/1927 | Sheetz |
| D75,971 S | 8/1928 | Faubert et al. |
| 1,687,079 A | 10/1928 | Barker |
| 1,694,636 A | 12/1928 | Barker |
| 1,696,433 A | 12/1928 | Faubert et al. |
| 1,704,564 A | 3/1929 | Friedland |
| 1,705,109 A | 3/1929 | Essbach |
| 1,707,118 A | 3/1929 | Goldberg |
| 1,708,050 A | 4/1929 | Burlew |
| 1,720,017 A | 7/1929 | Touchstone |
| 1,724,955 A | 8/1929 | Mitchell |
| 1,728,956 A | 9/1929 | Darmitzel |
| 1,741,143 A | 12/1929 | Chin |
| 1,764,130 A | 6/1930 | Vardeman |
| 1,770,195 A | 7/1930 | Burlew |
| 1,796,893 A | 3/1931 | McVeigh |
| 1,797,946 A | 3/1931 | Eichel |
| 1,801,915 A | 4/1931 | Gray |
| 1,817,585 A | 8/1931 | Samuel |
| 1,833,555 A | 11/1931 | Ball et al. |
| 1,860,924 A | 5/1932 | Cooke |
| 1,861,347 A | 5/1932 | Johnson |
| 1,863,389 A | 6/1932 | Anderson |
| 1,868,368 A | 7/1932 | Reese |
| 1,868,893 A | 7/1932 | Gentle |
| 1,872,832 A | 8/1932 | Silverberg |
| D88,805 S | 12/1932 | MacInnis |
| 1,891,864 A | 12/1932 | Barrett |
| 1,892,068 A | 12/1932 | Metzler |
| 1,901,646 A | 3/1933 | Hicks |
| 1,903,161 A | 3/1933 | Barkan |
| 1,907,286 A | 5/1933 | Chott |
| 1,910,414 A | 5/1933 | Varga |
| 1,924,152 A | 8/1933 | Coney et al. |
| 1,924,337 A | 8/1933 | Troupa |
| 1,927,365 A | 9/1933 | Frolio |
| 1,928,328 A | 9/1933 | Carpentier |
| 1,935,099 A | 11/1933 | Bluhm |
| 1,963,389 A | 6/1934 | Vardeman |
| 1,965,009 A | 7/1934 | Stevens |
| 2,083,217 A | 7/1934 | Brothers et al. |
| 1,993,662 A | 3/1935 | Green |
| 2,003,243 A | 5/1935 | Campbell et al. |
| 2,029,031 A | 1/1936 | Novick |
| D99,352 S | 4/1936 | Grapp |
| 2,039,278 A | 5/1936 | Blanchard |
| 2,042,239 A | 5/1936 | Planding |
| 2,049,956 A | 8/1936 | Greenberg |
| 2,059,914 A | 11/1936 | Rosenberg |
| 2,079,728 A | 5/1937 | Amoid |
| 2,083,595 A | 6/1937 | Clarren |
| 2,088,839 A | 8/1937 | Coney et al. |
| 2,093,007 A | 9/1937 | Chott |
| 2,117,174 A | 5/1938 | Jones |
| 2,122,619 A | 7/1938 | McMath |
| 2,123,407 A | 7/1938 | Dullea |
| 2,125,783 A | 8/1938 | Heeman |
| 2,129,082 A | 9/1938 | Byrer |
| 2,139,245 A | 12/1938 | Ogden |
| 2,140,307 A | 12/1938 | Belaschk et al. |
| 2,141,969 A | 12/1938 | Benz |
| 2,146,455 A | 2/1939 | Tepper |
| 2,149,425 A | 3/1939 | Draemann |
| 2,149,950 A | 3/1939 | Axline |
| 2,154,352 A | 4/1939 | Peterson |
| 2,154,846 A | 4/1939 | Heymann et al. |
| 2,155,473 A | 4/1939 | Coleman |
| 2,171,591 A | 9/1939 | Minich |
| 2,172,624 A | 9/1939 | Robert |
| 2,176,309 A | 10/1939 | Love et al. |
| 2,179,266 A | 11/1939 | Luckenbill |
| 2,189,175 A | 2/1940 | Jackson |
| 2,196,284 A | 4/1940 | Ackerman |
| 2,206,726 A | 7/1940 | Lasater |
| D122,815 S | 10/1940 | Crosby |
| 2,217,439 A | 10/1940 | Fuller |
| 2,218,072 A | 10/1940 | Runnels |
| 2,219,753 A | 10/1940 | Seguin |
| 2,220,053 A | 10/1940 | Pruner |
| 2,225,331 A | 12/1940 | Campbell |
| 2,226,145 A | 12/1940 | Smith |
| 2,233,936 A | 3/1941 | Campbell |
| 2,242,743 A | 5/1941 | Brown |
| 2,244,615 A | 6/1941 | Garcin |
| 2,244,699 A | 6/1941 | Hosey |
| 2,246,867 A | 6/1941 | Thomas et al. |
| 2,253,210 A * | 8/1941 | Psiharis .................. 601/139 |
| 2,253,910 A | 8/1941 | Luenz |
| 2,254,365 A | 9/1941 | Griffith et al. |
| 2,266,195 A | 12/1941 | Hallock |
| 2,274,042 A | 2/1942 | Cosby |
| 2,279,355 A | 4/1942 | Wilensky |
| 2,283,686 A | 5/1942 | McCune |
| 2,294,900 A | 9/1942 | Fuller |
| 2,312,828 A | 3/1943 | Adamsson |
| 2,326,632 A | 8/1943 | Friedman |
| 2,328,998 A | 9/1943 | Radford |
| 2,364,205 A | 12/1944 | Fuller |
| 2,418,485 A | 4/1947 | Shipley |
| 2,435,421 A | 2/1948 | Blair |
| 2,438,268 A | 3/1948 | Bressler |
| 2,443,297 A | 6/1948 | Bressler |
| 2,443,461 A | 6/1948 | Kempster |
| 2,473,773 A | 6/1949 | West |
| 2,476,201 A | 7/1949 | Ligoure |
| 2,483,503 A | 10/1949 | Pollack |
| 2,512,059 A | 6/1950 | Heaussar |
| 2,518,765 A | 8/1950 | Ecker |
| 2,516,491 A | 9/1950 | Swastek |
| 2,534,086 A | 12/1950 | Vosbikain et al. |
| 2,545,814 A | 3/1951 | Kempster |
| D162,941 S | 4/1951 | Ehman |
| 2,574,654 A | 11/1951 | Moore |
| 2,583,750 A | 1/1952 | Runnals |
| 2,584,735 A | 2/1952 | Pancoast |
| 2,600,136 A | 6/1952 | Staunt |
| 2,631,320 A | 3/1953 | Bressler |
| 2,637,870 A | 5/1953 | Cohen |
| 2,650,383 A | 9/1953 | Bressler |
| 2,676,350 A | 4/1954 | Bressler |
| 2,685,703 A | 8/1954 | Dellenbach |
| 2,702,914 A | 3/1955 | Kittle et al. |
| 2,722,031 A | 11/1955 | Bressler |
| 2,790,441 A | 4/1957 | Oderman |
| 2,807,820 A | 10/1957 | Dinhofer |
| 2,819,482 A | 1/1958 | Appligate |
| 2,939,522 A | 6/1960 | Morely et al. |
| 2,987,742 A | 6/1961 | Kittle et al. |
| 3,007,441 A | 11/1961 | Eyer |
| 3,016,554 A | 1/1962 | Peterson |
| 3,050,072 A | 8/1962 | Diener |
| 3,082,457 A | 3/1963 | Lucibello et al. |
| 3,103,027 A | 9/1963 | Birch |
| 3,103,680 A | 9/1963 | Krichmar |
| 3,128,487 A | 4/1964 | Vallis |

(56) References Cited

U.S. PATENT DOCUMENTS

| | | |
|---|---|---|
| 3,129,449 A | 4/1964 | Cyzer |
| 3,133,546 A | 5/1964 | Dent |
| 3,152,349 A | 10/1964 | Brennesholtz |
| 3,183,538 A | 5/1965 | Hubner |
| 3,188,672 A | 6/1965 | Gary |
| 3,188,673 A | 6/1965 | Newman |
| 3,195,537 A | 7/1965 | Blasi |
| 3,196,229 A | 7/1965 | Glass |
| D201,867 S | 8/1965 | Newman |
| 3,199,139 A | 8/1965 | Vallis |
| 3,230,562 A | 1/1966 | Birch |
| 3,242,516 A | 3/1966 | Cantor |
| 3,253,292 A | 5/1966 | Herschensohn |
| 3,258,805 A | 7/1966 | Rossnan |
| 3,261,354 A | 7/1966 | Shpuntoff |
| 3,295,156 A | 1/1967 | Brant |
| 3,302,230 A | 2/1967 | Poppelman |
| 3,316,576 A | 5/1967 | Urbush |
| 3,327,339 A | 6/1967 | Lemelson |
| 3,337,893 A | 8/1967 | Fine et al. |
| 3,359,588 A | 12/1967 | Kobler |
| 3,359,759 A | 12/1967 | Kramer et al. |
| 3,378,870 A | 4/1968 | Matsunaga |
| 3,398,421 A | 8/1968 | Rashbaum |
| 3,403,070 A | 9/1968 | Lewis, Jr. |
| 3,411,979 A | 11/1968 | Lewis, Jr. |
| D213,669 S | 4/1969 | Miller |
| 3,465,751 A | 9/1969 | Powers |
| RE26,688 E | 10/1969 | Lemelson |
| 3,488,788 A | 1/1970 | Robinson |
| 3,491,396 A | 1/1970 | Eannarino et al. |
| 3,553,759 A | 1/1971 | Kramer et al. |
| 3,583,019 A | 6/1971 | Conklin, Jr. |
| 3,613,143 A | 10/1971 | Muhler et al. |
| 3,619,845 A | 11/1971 | Partridge et al. |
| 3,633,237 A | 1/1972 | Bagube |
| 3,677,264 A | 7/1972 | Brockman |
| 3,678,528 A | 7/1972 | Haije |
| 3,722,020 A | 3/1973 | Hills |
| 3,742,549 A | 7/1973 | Scopp et al. |
| 3,754,295 A | 8/1973 | Hyman |
| 3,792,504 A | 2/1974 | Smith |
| 3,914,081 A | 10/1975 | Aoko |
| D239,221 S | 3/1976 | Wasserman |
| 3,969,783 A | 7/1976 | Shipman |
| 3,977,084 A | 8/1976 | Sloan |
| 3,992,747 A | 11/1976 | Hufton |
| 4,020,521 A | 5/1977 | Velasquez |
| 4,031,587 A | 6/1977 | Dietrich |
| 4,033,008 A | 7/1977 | Warren et al. |
| 4,081,876 A | 4/1978 | Pugh |
| 4,081,877 A | 4/1978 | Vitale |
| 4,083,078 A | 4/1978 | Shimizu |
| D248,696 S | 8/1978 | Greenberg |
| 4,115,893 A | 9/1978 | Nakata et al. |
| 4,115,894 A | 9/1978 | Peterson |
| 4,128,910 A | 12/1978 | Nakata et al. |
| 4,150,457 A | 4/1979 | Larson |
| 4,156,620 A | 5/1979 | Clemens |
| 4,220,144 A | 9/1980 | Balais |
| 4,240,452 A | 12/1980 | Jean |
| 4,263,691 A | 4/1981 | Pakarnseree |
| D259,976 S | 7/1981 | Seelig |
| 4,277,862 A | 7/1981 | Weideman |
| 4,283,808 A | 8/1981 | Beebe |
| 4,288,883 A | 9/1981 | Dolinsky |
| 4,299,208 A | 11/1981 | Blanc |
| 4,356,585 A | 11/1982 | Protell et al. |
| 4,364,142 A | 12/1982 | Pangle |
| 4,391,951 A | 7/1983 | Scheetz |
| 4,403,623 A | 9/1983 | Mark |
| 4,406,032 A | 9/1983 | Diamant |
| 4,416,166 A | 11/1983 | Jannard et al. |
| 4,428,091 A | 1/1984 | Janssen |
| D272,688 S | 2/1984 | Stocchi |
| D272,689 S | 2/1984 | Stocchi |
| D272,690 S | 2/1984 | Stocchi |
| 4,432,114 A | 2/1984 | Goudsmit |
| 4,432,729 A | 2/1984 | Fattaleh |
| D273,635 S | 5/1984 | Stocchi |
| 4,455,704 A | 6/1984 | Williams |
| 4,461,285 A | 7/1984 | Courtin |
| 4,472,853 A | 9/1984 | Rauch |
| 4,476,280 A | 10/1984 | Poppe et al. |
| D276,193 S | 11/1984 | Tanabe et al. |
| 4,480,351 A | 11/1984 | Koffler |
| 4,488,327 A | 12/1984 | Snider |
| 4,488,328 A | 12/1984 | Hyman |
| 4,517,701 A | 5/1985 | Stanford, Jr. |
| 4,520,526 A | 6/1985 | Peters |
| 4,525,531 A | 6/1985 | Zukosky et al. |
| 4,534,340 A | 8/1985 | Kerr et al. |
| 4,543,679 A | 10/1985 | Rosofsky et al. |
| 4,545,087 A | 10/1985 | Nahum |
| 4,570,282 A | 2/1986 | Kaufman et al. |
| 4,573,920 A | 3/1986 | D'Argembeau |
| 4,585,416 A | 4/1986 | DeNiro et al. |
| 4,603,166 A | 7/1986 | Poppe et al. |
| D285,263 S | 8/1986 | Hill |
| 4,610,043 A | 9/1986 | Vezjak |
| 4,616,064 A | 10/1986 | Zukosky et al. |
| 4,617,342 A | 10/1986 | Poppe et al. |
| 4,617,694 A | 10/1986 | Bori |
| 4,623,495 A | 11/1986 | Degoix et al. |
| D287,072 S | 12/1986 | Pfleger |
| 4,628,564 A | 12/1986 | Youssef |
| 4,633,542 A | 1/1987 | Taravel |
| 4,646,381 A | 3/1987 | Weihrauch |
| D289,703 S | 5/1987 | Yaffe |
| D289,704 S | 5/1987 | Marthaler et al. |
| 4,672,706 A | 6/1987 | Hill |
| 4,691,405 A | 9/1987 | Reed |
| 4,694,844 A | 9/1987 | Berl et al. |
| D292,448 S | 10/1987 | Vianello |
| 4,712,267 A | 12/1987 | Cheng |
| 4,712,304 A | 12/1987 | Sanelli |
| 4,721,021 A | 1/1988 | Kusznir |
| 4,734,230 A | 3/1988 | Rhodes, Jr. et al. |
| 4,739,536 A | 4/1988 | Bandera et al. |
| 4,749,233 A | 6/1988 | Weihrauch |
| 4,776,054 A | 10/1988 | Rauch |
| 4,780,924 A | 11/1988 | Hansen et al. |
| 4,800,608 A | 1/1989 | Key |
| 4,802,255 A | 2/1989 | Bruer et al. |
| 4,827,550 A | 5/1989 | Graham et al. |
| 4,827,551 A | 5/1989 | Maser et al. |
| 4,829,621 A | 5/1989 | Phenegar |
| 4,833,194 A | 5/1989 | Kuan et al. |
| 4,845,795 A | 7/1989 | Crawford et al. |
| 4,847,936 A | 7/1989 | Moglianesi et al. |
| 4,852,202 A | 8/1989 | Ledwitz |
| 4,864,676 A | 9/1989 | Schaiper |
| 4,880,382 A | 11/1989 | Moret et al. |
| 4,882,803 A | 11/1989 | Rogers et al. |
| 4,894,880 A | 1/1990 | Aznavoorian |
| 4,949,457 A | 8/1990 | Burout, III |
| 5,005,246 A | 4/1991 | Yen-Hui |
| 5,014,383 A | 5/1991 | Costar |
| 5,020,179 A | 6/1991 | Scherer |
| 5,021,475 A | 6/1991 | Isayev |
| 5,027,463 A | 7/1991 | Daub |
| 5,027,511 A | 7/1991 | Miller |
| 5,027,796 A | 7/1991 | Linzey |
| 5,033,150 A | 7/1991 | Gross et al. |
| 5,034,450 A | 7/1991 | Betz et al. |
| D319,148 S | 8/1991 | Emily |
| 5,040,260 A | 8/1991 | Michaels |
| 5,046,213 A | 9/1991 | Curtis et al. |
| 5,052,071 A | 10/1991 | Halm |
| 5,054,154 A | 10/1991 | Schiffer et al. |
| 5,070,567 A | 12/1991 | Holland |
| 5,088,145 A | 2/1992 | Whitefield |
| D324,775 S | 3/1992 | Kreisher et al. |
| 5,114,214 A | 5/1992 | Barman |

(56) References Cited

U.S. PATENT DOCUMENTS

| | | |
|---|---|---|
| 5,119,522 A | 6/1992 | Potts |
| 5,121,520 A | 6/1992 | Brice |
| 5,137,039 A | 8/1992 | Klinkhammer |
| 5,144,712 A | 9/1992 | Hansel et al. |
| 5,148,567 A | 9/1992 | Daub |
| D330,286 S | 10/1992 | Curtis et al. |
| 5,160,194 A | 11/1992 | Feldman |
| 5,170,525 A | 12/1992 | Cafaro |
| 5,171,633 A | 12/1992 | Muramoto et al. |
| 5,184,368 A | 2/1993 | Holland |
| 5,212,848 A | 5/1993 | Geyer |
| 5,226,197 A | 7/1993 | Nack |
| 5,226,206 A | 7/1993 | Davidovitz et al. |
| 5,228,466 A | 7/1993 | Klinkhammer |
| 5,230,118 A | 7/1993 | Chamma |
| 5,242,235 A | 9/1993 | Li |
| 5,249,327 A | 10/1993 | Hing |
| 5,261,665 A | 11/1993 | Downey |
| D342,160 S | 12/1993 | Curtis et al. |
| D342,162 S | 12/1993 | Curtis et al. |
| 5,273,425 A | 12/1993 | Hoagland |
| 5,274,870 A | 1/1994 | Stollman |
| 5,283,921 A * | 2/1994 | Ng .................. 15/22.1 |
| D345,054 S | 3/1994 | Spence, Jr. |
| 5,291,878 A | 3/1994 | Lombardo et al. |
| 5,305,489 A | 4/1994 | Lage |
| 5,305,490 A | 4/1994 | Lundgren |
| 5,313,909 A | 5/1994 | Tseng et al. |
| 5,323,795 A | 6/1994 | Berens |
| 5,325,560 A | 7/1994 | Pavone et al. |
| 5,331,704 A | 7/1994 | Rosen et al. |
| 5,334,646 A | 8/1994 | Chen |
| 5,335,389 A | 8/1994 | Curtis et al. |
| D350,851 S | 9/1994 | Spence, Jr. |
| 5,347,676 A | 9/1994 | Saitoh |
| 5,348,473 A | 9/1994 | Kivlighan |
| 5,349,716 A | 9/1994 | Miller |
| 5,350,219 A | 9/1994 | Shou-Jen |
| D351,732 S | 10/1994 | Dair et al. |
| 5,351,358 A | 10/1994 | Larrimore |
| 5,353,464 A | 10/1994 | Atkins et al. |
| 5,355,546 A | 10/1994 | Scheier et al. |
| 5,360,025 A | 11/1994 | Klinkhammer |
| 5,360,026 A | 11/1994 | Klinkhammer |
| 5,373,602 A | 12/1994 | Bang |
| 5,390,572 A | 2/1995 | Gakhar et al. |
| 5,392,483 A | 2/1995 | Heinzelman et al. |
| 5,398,368 A | 3/1995 | Elder |
| 5,398,369 A | 3/1995 | Heinzelman et al. |
| 5,435,032 A | 7/1995 | McDougall |
| D360,760 S | 8/1995 | Halm |
| 5,446,940 A | 9/1995 | Curtis et al. |
| 5,454,133 A | 10/1995 | Garnet |
| 5,483,722 A | 1/1996 | Scheier et al. |
| 5,511,275 A | 4/1996 | Volpenhein et al. |
| 5,533,227 A | 7/1996 | Ito et al. |
| 5,535,474 A | 7/1996 | Salazar |
| 5,539,949 A | 7/1996 | Stanton |
| 5,584,690 A | 12/1996 | Maassarani |
| 5,604,951 A | 2/1997 | Shipp |
| 5,617,601 A | 4/1997 | McDougall |
| 5,617,603 A | 4/1997 | Mei |
| 5,628,082 A | 5/1997 | Moskovich |
| 5,630,244 A | 5/1997 | Chang |
| 5,651,158 A | 7/1997 | Halm |
| 5,669,097 A | 9/1997 | Klinkhammer |
| D390,706 S | 2/1998 | Hohlbein et al. |
| D391,769 S | 3/1998 | Kling et al. |
| 5,723,543 A | 3/1998 | Modic |
| 5,735,011 A | 4/1998 | Asher |
| 5,735,864 A | 4/1998 | Heisinger, Jr. |
| 5,742,972 A | 4/1998 | Bredall et al. |
| 5,758,380 A | 6/1998 | Vrignaud |
| 5,758,383 A | 6/1998 | Hohlbein |
| 5,761,759 A | 6/1998 | Leversby et al. |
| 5,774,923 A | 7/1998 | Halm |
| 5,781,958 A | 7/1998 | Meessmann et al. |
| 5,802,656 A | 9/1998 | Dawson et al. |
| 5,810,856 A | 9/1998 | Tveras |
| 5,813,079 A | 9/1998 | Halm |
| D399,349 S | 10/1998 | Barth |
| D401,069 S | 11/1998 | Lamond et al. |
| 5,836,033 A | 11/1998 | Berge |
| 5,839,149 A | 11/1998 | Scheier et al. |
| D402,116 S | 12/1998 | Magloff et al. |
| 5,842,249 A | 12/1998 | Sato |
| D403,510 S | 1/1999 | Menke et al. |
| D404,205 S | 1/1999 | Hohlbein |
| D404,206 S | 1/1999 | Hohlbein |
| D407,221 S | 3/1999 | Van Gelder |
| D407,222 S | 3/1999 | Van Gelder |
| D407,223 S | 3/1999 | Van Gelder |
| 5,876,207 A | 3/1999 | Sundius et al. |
| 5,896,614 A | 4/1999 | Flewitt |
| 5,920,941 A | 7/1999 | Iannota |
| 5,930,860 A * | 8/1999 | Shipp .................. 15/110 |
| 5,946,758 A | 9/1999 | Hohlbein et al. |
| 5,946,759 A | 9/1999 | Cann |
| 5,966,771 A | 10/1999 | Stroud |
| 5,970,564 A | 10/1999 | Inns et al. |
| 5,980,542 A | 11/1999 | Saldivas |
| 5,984,935 A | 11/1999 | Welt et al. |
| 5,987,688 A | 11/1999 | Roberts et al. |
| 5,991,958 A | 11/1999 | Hohlbein |
| 5,991,959 A | 11/1999 | Raven et al. |
| 6,006,394 A | 12/1999 | Bredall et al. |
| 6,015,293 A | 1/2000 | Rimkus |
| D420,515 S | 2/2000 | Van Gelder |
| D421,844 S | 3/2000 | Stark et al. |
| 6,032,315 A | 3/2000 | Liebel |
| 6,032,322 A | 3/2000 | Forsline |
| 6,041,467 A | 3/2000 | Roberts et al. |
| 6,041,468 A | 3/2000 | Chen et al. |
| D423,787 S | 5/2000 | Musciano |
| 6,065,890 A | 5/2000 | Weitz |
| 6,067,684 A | 5/2000 | Kweon |
| 6,073,299 A | 6/2000 | Hohlbein |
| 6,085,379 A | 7/2000 | Stafford |
| D428,702 S | 8/2000 | Van Gelder |
| 6,098,233 A | 8/2000 | Chen |
| 6,099,309 A | 8/2000 | Cardarelli |
| 6,102,923 A | 8/2000 | Murayama |
| 6,105,191 A | 8/2000 | Chen et al. |
| 6,108,854 A | 8/2000 | Dingert |
| 6,115,870 A | 9/2000 | Solanki et al. |
| 6,119,296 A | 9/2000 | Noe et al. |
| 6,126,533 A | 10/2000 | Johnson et al. |
| 6,138,316 A | 10/2000 | Weihrauch |
| 6,151,745 A | 11/2000 | Roberts et al. |
| D434,563 S | 12/2000 | Lim et al. |
| D434,565 S | 12/2000 | Bojar |
| D434,908 S | 12/2000 | Bojar |
| 6,161,245 A | 12/2000 | Weihrauch |
| 6,178,582 B1 | 1/2001 | Halm |
| 6,185,779 B1 | 2/2001 | Kramer |
| 6,209,164 B1 | 4/2001 | Sato |
| 6,219,874 B1 | 4/2001 | Van Gelder et al. |
| 6,254,390 B1 | 7/2001 | Wagner |
| 6,260,227 B1 | 7/2001 | Fulpo et al. |
| 6,276,019 B1 | 8/2001 | Leversby et al. |
| 6,276,021 B1 | 8/2001 | Hohlbein |
| 6,308,364 B1 | 10/2001 | Arone |
| 6,308,365 B1 | 10/2001 | Huang |
| 6,311,358 B1 | 11/2001 | Soetewey et al. |
| 6,311,360 B1 | 11/2001 | Lanvers |
| 6,314,605 B1 | 11/2001 | Solanki et al. |
| 6,314,606 B1 | 11/2001 | Hohlbein |
| 6,319,332 B1 | 11/2001 | Gavney, Jr. et al. |
| 6,322,573 B1 | 11/2001 | Murayama |
| 6,334,232 B1 | 1/2002 | Sato |
| 6,345,405 B1 | 2/2002 | Brackin |
| 6,360,395 B2 | 3/2002 | Blaustein et al. |
| D456,139 S | 4/2002 | Hohlbein |
| 6,371,294 B1 | 4/2002 | Blaustein et al. |

(56) References Cited

U.S. PATENT DOCUMENTS

| | | |
|---|---|---|
| 6,374,448 B2 | 4/2002 | Seifert |
| D459,087 S | 6/2002 | Pfleger |
| 6,408,476 B1 | 6/2002 | Cann |
| D461,959 S | 8/2002 | Chan et al. |
| D463,131 S | 9/2002 | Winter et al. |
| 6,442,786 B2 | 9/2002 | Halm et al. |
| 6,442,787 B2 | 9/2002 | Hohlbein |
| 6,446,295 B1 | 9/2002 | Calabrese |
| 6,463,618 B1 | 10/2002 | Zimmer |
| 6,463,619 B2 | 10/2002 | Gavney, Jr. |
| 6,505,373 B2 | 1/2003 | Van Gelder et al. |
| 6,510,575 B2 | 1/2003 | Calabrese |
| 6,513,182 B1 | 2/2003 | Calabrese et al. |
| 6,514,445 B1 | 2/2003 | Cann et al. |
| 6,553,604 B1 | 4/2003 | Braun et al. |
| 6,554,614 B1 | 4/2003 | Dubbe et al. |
| 6,571,417 B1 | 6/2003 | Gavney, Jr. et al. |
| D477,465 S | 7/2003 | Reilly et al. |
| 6,599,048 B2 | 7/2003 | Kuo |
| D478,211 S | 8/2003 | Ping |
| 6,612,770 B2 | 9/2003 | Aoyoma |
| D482,199 S | 11/2003 | DeSalvo |
| 6,654,979 B2 | 12/2003 | Calabrese |
| 6,658,688 B2 | 12/2003 | Gavney, Jr. |
| 6,668,418 B2 | 12/2003 | Bastien |
| 6,671,919 B2 | 1/2004 | Davis |
| D486,649 S | 2/2004 | Sprosta et al. |
| 6,693,804 B2 | 2/2004 | Suzuki |
| 6,708,364 B1 | 3/2004 | Huber |
| 6,729,789 B2 | 5/2004 | Gordon |
| 6,792,642 B2 | 9/2004 | Wagstaff |
| 6,807,703 B2 | 10/2004 | Van Gelder et al. |
| 6,810,551 B1 | 11/2004 | Weihrauch |
| 6,817,054 B2 | 11/2004 | Moskovich et al. |
| 6,820,299 B2 | 11/2004 | Gavney, Jr. |
| 6,820,300 B2 | 11/2004 | Gavney, Jr. |
| 6,823,554 B1 | 11/2004 | Braun et al. |
| 6,859,969 B2 | 3/2005 | Gavney, Jr. |
| 6,865,767 B1 | 3/2005 | Gavney, Jr. |
| D503,538 S | 4/2005 | DeSalvo |
| 6,886,207 B1 | 5/2005 | Solanki |
| 6,895,624 B2 | 5/2005 | Fischer et al. |
| 6,895,629 B1 | 5/2005 | Wenzler |
| D506,871 S | 7/2005 | Winkler et al. |
| D506,872 S | 7/2005 | Winkler et al. |
| 6,938,293 B2 | 9/2005 | Eliav et al. |
| 6,944,903 B2 | 9/2005 | Gavney, Jr. |
| 6,966,093 B2 | 11/2005 | Eliav et al. |
| 6,996,870 B2 * | 2/2006 | Hohlbein ........................ 15/110 |
| D517,812 S | 3/2006 | Hohlbein et al. |
| 7,020,928 B2 | 4/2006 | Hohlbein |
| 7,024,720 B2 | 4/2006 | Moskovich et al. |
| 7,036,180 B2 | 5/2006 | Hanlon |
| 7,047,589 B2 | 5/2006 | Gavney, Jr. |
| 7,051,394 B2 | 5/2006 | Gavney, Jr. |
| RE39,185 E | 7/2006 | Noe et al. |
| 7,069,615 B2 | 7/2006 | Gavney, Jr. |
| 7,073,225 B1 | 7/2006 | Ford |
| D531,809 S | 11/2006 | Li |
| 7,137,163 B2 | 11/2006 | Gatzemeyer et al. |
| 7,143,462 B2 | 12/2006 | Hohlbein |
| 7,181,799 B2 | 2/2007 | Gavney, Jr. et al. |
| 7,322,067 B2 | 1/2008 | Hohlbein |
| 7,707,676 B2 | 5/2010 | Solanki |
| 7,950,100 B2 | 5/2011 | Hohlbein |
| 2001/0014991 A1 | 8/2001 | Halm et al. |
| 2001/0039689 A1 | 11/2001 | Gavney |
| 2002/0017003 A1 | 2/2002 | Kramer et al. |
| 2002/0084550 A1 | 7/2002 | Roberts et al. |
| 2002/0124337 A1 | 9/2002 | Calabrese et al. |
| 2002/0138928 A1 | 10/2002 | Calabrese |
| 2002/0152563 A1 | 10/2002 | Sato |
| 2003/0009837 A1 | 1/2003 | Cann |
| 2003/0019060 A1 | 1/2003 | Gavney |
| 2003/0033680 A1 | 2/2003 | Davies et al. |
| 2003/0033682 A1 | 2/2003 | Davies et al. |
| 2003/0077107 A1 | 4/2003 | Kuo |
| 2003/0115699 A1 | 6/2003 | Wagstaff |
| 2003/0116884 A1 | 6/2003 | Wagstaff |
| 2003/0140437 A1 | 7/2003 | Eliav et al. |
| 2003/0140440 A1 | 7/2003 | Gavney, Jr. |
| 2003/0182743 A1 | 10/2003 | Gatzenmeyer |
| 2003/0182746 A1 | 10/2003 | Fattori et al. |
| 2003/0196283 A1 | 10/2003 | Eliav et al. |
| 2003/0213075 A1 | 11/2003 | Hui et al. |
| 2003/0229959 A1 | 12/2003 | Gavney, Jr. et al. |
| 2004/0006837 A1 | 1/2004 | Cann |
| 2004/0010869 A1 | 1/2004 | Fattori et al. |
| 2004/0025275 A1 | 2/2004 | Moskovich et al. |
| 2004/0031115 A1 | 2/2004 | Gavney |
| 2004/0045105 A1 | 3/2004 | Eliav |
| 2004/0060132 A1 | 4/2004 | Gatzemeyer et al. |
| 2004/0060133 A1 | 4/2004 | Eliav |
| 2004/0060136 A1 | 4/2004 | Gatzemeyer et al. |
| 2004/0060137 A1 | 4/2004 | Eliav |
| 2004/0087882 A1 | 5/2004 | Roberts et al. |
| 2004/0134007 A1 | 7/2004 | Davies |
| 2004/0154112 A1 | 8/2004 | Braun et al. |
| 2004/0168271 A1 | 9/2004 | McDougall |
| 2004/0177462 A1 | 9/2004 | Brown et al. |
| 2004/0221409 A1 | 11/2004 | Gavney, Jr. |
| 2004/0231076 A1 | 11/2004 | Gavney, Jr. |
| 2004/0231082 A1 | 11/2004 | Gavney, Jr. |
| 2004/0237226 A1 | 12/2004 | Hohlbein et al. |
| 2004/0237236 A1 | 12/2004 | Gavneym, Jr. |
| 2004/0237995 A1 | 12/2004 | Mualem et al. |
| 2004/0255416 A1 * | 12/2004 | Hohlbein ........................ 15/106 |
| 2004/0255427 A1 | 12/2004 | Gavney |
| 2004/0261207 A1 | 12/2004 | Gavney |
| 2005/0000043 A1 | 1/2005 | Chan et al. |
| 2005/0000049 A1 * | 1/2005 | Hohlbein ........................ 15/111 |
| 2005/0015901 A1 | 1/2005 | Gavney, Jr. |
| 2005/0015904 A1 | 1/2005 | Gavney |
| 2005/0038461 A1 | 2/2005 | Phillips |
| 2005/0049155 A1 | 3/2005 | Gavney et al. |
| 2005/0060826 A1 | 3/2005 | Gavney |
| 2005/0066456 A1 | 3/2005 | Gavney |
| 2005/0086753 A1 | 4/2005 | Roberts et al. |
| 2005/0091773 A1 | 5/2005 | Gavney, Jr. |
| 2005/0155172 A1 | 7/2005 | Gavney, Jr. |
| 2005/0166341 A1 | 8/2005 | Solanki |
| 2005/0166344 A1 | 8/2005 | Hohlbein et al. |
| 2005/0198757 A1 | 9/2005 | Gavney, Jr. et al. |
| 2005/0210612 A1 | 9/2005 | Hohlbein et al. |
| 2005/0210613 A1 | 9/2005 | Wagstaff |
| 2005/0229339 A1 | 10/2005 | Gavney, Jr. et al. |
| 2005/0273954 A1 | 12/2005 | Gavney, Jr. |
| 2005/0278883 A1 | 12/2005 | Hohlbein |
| 2006/0010628 A1 | 1/2006 | Moskovich |
| 2006/0021170 A1 | 2/2006 | Gavney, Jr. |
| 2006/0026784 A1 | 2/2006 | Moskovich et al. |
| 2006/0047292 A1 | 3/2006 | Reed |
| 2006/0052806 A1 | 3/2006 | Xi et al. |
| 2006/0059642 A1 | 3/2006 | Solanki |
| 2006/0064833 A1 * | 3/2006 | Jacobs ........................ 15/110 |
| 2006/0085931 A1 | 4/2006 | Roberts et al. |
| 2006/0085932 A1 | 4/2006 | Santos |
| 2006/0107478 A1 | 5/2006 | Boucherie |
| 2006/0117506 A1 | 6/2006 | Gavney, Jr. et al. |
| 2006/0129171 A1 | 6/2006 | Moskovich |
| 2006/0130257 A1 | 6/2006 | Cann |
| 2006/0195995 A1 | 9/2006 | Moskovich et al. |
| 2006/0200922 A1 | 9/2006 | Hohlbein |
| 2006/0200925 A1 | 9/2006 | Moskovich |
| 2006/0230563 A1 | 10/2006 | Gavney, Jr. |
| 2006/0236477 A1 | 10/2006 | Gavney, Jr. |
| 2006/0240380 A1 | 10/2006 | Chenvainu et al. |
| 2006/0242778 A1 | 11/2006 | Solanki |
| 2006/0248668 A1 | 11/2006 | Rosenblood et al. |
| 2006/0272113 A1 | 12/2006 | Cato et al. |
| 2006/0288510 A1 | 12/2006 | Georgi et al. |
| 2007/0033755 A1 | 2/2007 | Gavney, Jr. |
| 2007/0074361 A1 | 4/2007 | Gavney, Jr. |
| 2007/0101525 A1 * | 5/2007 | Hohlbein ........................ 15/106 |

(56) References Cited

U.S. PATENT DOCUMENTS

| | | |
|---|---|---|
| 2007/0234496 A1 | 10/2007 | Roberts et al. |
| 2009/0013484 A1 | 1/2009 | Roberts et al. |
| 2009/0025162 A1 | 1/2009 | Chan |
| 2009/0044357 A1 | 2/2009 | Chan et al. |
| 2009/0193604 A1 | 8/2009 | Pfenniger et al. |

FOREIGN PATENT DOCUMENTS

| | | |
|---|---|---|
| CN | 1182354 A | 5/1998 |
| CN | 1207655 A | 2/1999 |
| CN | ZL99225704.2 | 2/1999 |
| CN | 1231586 A | 10/1999 |
| CN | 1248151 A | 11/1999 |
| CN | 99225704.2 | 11/1999 |
| CN | 1131688 C | 12/2003 |
| CN | 1131689 C | 12/2003 |
| DE | 188848 | 4/1956 |
| DE | 2311043 | 9/1974 |
| DE | 24 02 785 | 3/1979 |
| DE | 29 30 459 | 2/1981 |
| DE | 31 14507 A1 | 3/1983 |
| DE | 36 28722 A1 | 2/1988 |
| DE | 3737223 | 5/1989 |
| DE | 9318148.5 | 5/1994 |
| DE | 9400231.2 | 5/1994 |
| DE | 9400926 | 5/1994 |
| DE | 19708875 C1 | 5/1998 |
| DE | 698 02 741 T2 | 10/1998 |
| DE | 29816488 U1 | 12/1998 |
| DE | 10122987 A1 | 11/2002 |
| EP | 0 165 546 A2 | 12/1985 |
| EP | 0 336 641 | 10/1989 |
| EP | 0 360 766 A1 | 3/1990 |
| EP | 0 580 406 A1 | 1/1994 |
| EP | 0577656 | 1/1994 |
| EP | 0 716 573 B1 | 1/1997 |
| EP | 0 708 609 B1 | 12/1998 |
| EP | 0 768 831 B1 | 11/1999 |
| EP | 1 034 721 | 9/2000 |
| EP | 1080664 | 3/2001 |
| EP | 0 957 707 B1 | 1/2002 |
| EP | 1 308 108 | 5/2003 |
| EP | 1 350 442 | 8/2003 |
| EP | 1187541 B1 | 8/2004 |
| FR | 1075171 | 10/1854 |
| FR | 442832 | 9/1912 |
| FR | 567187 | 2/1924 |
| FR | 792476 | 12/1935 |
| FR | 920155 | 3/1947 |
| FR | 936529 | 6/1948 |
| FR | 1431088 | 1/1966 |
| FR | 2196782 A1 | 3/1974 |
| FR | 2232284 | 1/1975 |
| FR | 2541100 | 8/1984 |
| FR | 2559361 | 8/1985 |
| FR | 2 594 307 A1 | 4/1987 |
| FR | 2636818 A1 | 9/1988 |
| FR | 2773961 | 7/1999 |
| FR | 2793136 A1 | 11/2000 |
| GB | 17643 | 4/1912 |
| GB | 471387 | 9/1937 |
| GB | 2137080 | 10/1984 |
| GB | 2036076 | 6/1990 |
| GB | 2371217 A | 7/2002 |
| GB | 2 391 462 | 2/2004 |
| IT | 592300 | 4/1959 |
| JP | 50-11769 | 2/1975 |
| JP | 55-102835 | 1/1979 |
| JP | 55099210 U | 7/1980 |
| JP | 60-122139 | 8/1985 |
| JP | 61-090877 | 5/1986 |
| JP | 64-12525 | 1/1989 |
| JP | 1-72128 | 5/1989 |
| JP | 2-119031 | 5/1990 |
| JP | 2-180203 | 7/1990 |
| JP | 2-98719 | 8/1990 |
| JP | 02-143036 U | 12/1990 |
| JP | 3-003226 | 1/1991 |
| JP | 4-18530 | 2/1992 |
| JP | 4-128627 | 11/1992 |
| JP | 5-069342 | 3/1993 |
| JP | 5-096597 | 4/1993 |
| JP | 5-12322 | 5/1993 |
| JP | 2533441 | 6/1996 |
| JP | 2533443 | 6/1996 |
| JP | 2533445 | 6/1996 |
| JP | 1997-140456 | 3/1997 |
| JP | 9140456 A | 3/1997 |
| JP | 9140456 A | 6/1997 |
| JP | 10-066704 | 3/1998 |
| JP | 2781861 | 5/1998 |
| JP | 11009341 A | 1/1999 |
| JP | 3063406 U | 8/1999 |
| JP | 11332651 | 12/1999 |
| JP | 2000-157338 | 6/2000 |
| JP | 3069418 | 7/2000 |
| JP | 2000-300345 | 10/2000 |
| JP | 2000-300347 | 10/2000 |
| JP | 2000-308522 | 11/2000 |
| JP | 2000-308524 | 11/2000 |
| JP | 2001299454 | 10/2001 |
| JP | 2001-314232 | 11/2001 |
| JP | 2002345560 A | 3/2002 |
| JP | 2002-142857 | 5/2002 |
| JP | 2002-223853 | 8/2002 |
| KR | 71844 | 6/1974 |
| SU | 1708283 | 1/1992 |
| TW | 330411 | 4/1998 |
| WO | WO94/05183 A1 | 6/1971 |
| WO | WO87/00032 A2 | 1/1987 |
| WO | WO91/05088 | 4/1991 |
| WO | WO 92/04589 | 3/1992 |
| WO | WO92/17092 A1 | 10/1992 |
| WO | WO92/17093 | 10/1992 |
| WO | WO93/14671 | 8/1993 |
| WO | WO94/09676 | 5/1994 |
| WO | WO94/09678 A1 | 5/1994 |
| WO | WO95/06420 A1 | 3/1995 |
| WO | WO96/01577 A1 | 1/1996 |
| WO | WO96/02165 | 2/1996 |
| WO | WO 96/15696 | 5/1996 |
| WO | WO96/20654 A1 | 7/1996 |
| WO | WO 96/23431 | 8/1996 |
| WO | WO 96/28994 | 9/1996 |
| WO | WO97/03587 A1 | 2/1997 |
| WO | WO97/07706 A3 | 3/1997 |
| WO | WO97/07707 A1 | 3/1997 |
| WO | WO97/10938 A1 | 3/1997 |
| WO | WO97/16995 A1 | 5/1997 |
| WO | WO97/20484 A1 | 6/1997 |
| WO | WO97/24048 A1 | 7/1997 |
| WO | WO97/25900 A1 | 7/1997 |
| WO | WO97/29663 A1 | 8/1997 |
| WO | WO98/03097 A1 | 1/1998 |
| WO | WO98/05239 | 2/1998 |
| WO | WO 98/05241 | 2/1998 |
| WO | WO 98/08458 | 3/1998 |
| WO | WO98/11843 A1 | 3/1998 |
| WO | WO 98/18364 | 5/1998 |
| WO | WO98/22000 A1 | 5/1998 |
| WO | WO99/23910 | 5/1999 |
| WO | WO99/37180 | 7/1999 |
| WO | WO99/37181 A1 | 7/1999 |
| WO | WO99/37182 A1 | 7/1999 |
| WO | WO99/44465 A1 | 9/1999 |
| WO | WO 99/49754 | 10/1999 |
| WO | WO 99/60886 A1 | 12/1999 |
| WO | WO00/15077 A2 | 3/2000 |
| WO | WO00/30495 A1 | 6/2000 |
| WO | WO 00/53054 | 9/2000 |
| WO | WO00/60980 A2 | 10/2000 |
| WO | WO 00/64307 | 11/2000 |
| WO | WO 00/76369 A2 | 12/2000 |

(56) References Cited

FOREIGN PATENT DOCUMENTS

| | | |
|---|---|---|
| WO | WO 00/76369 A3 | 12/2000 |
| WO | WO01/01817 A1 | 1/2001 |
| WO | WO 01/17433 | 3/2001 |
| WO | WO01/21036 A1 | 3/2001 |
| WO | WO0117433 * | 3/2001 ............ A46B 9/04 |
| WO | WO01/35792 A2 | 5/2001 |
| WO | WO 01/45573 | 6/2001 |
| WO | WO 02/062174 | 8/2002 |
| WO | WO03/015575 A1 | 2/2003 |
| WO | WO03/020076 A1 | 3/2003 |
| WO | WO03/030680 A1 | 4/2003 |
| WO | WO03/043459 A2 | 5/2003 |
| WO | WO03/075711 A1 | 9/2003 |
| WO | WO 03/086140 A1 | 10/2003 |
| WO | WO04/000155 A1 | 12/2003 |
| WO | WO 2004/014181 A1 | 2/2004 |
| WO | WO2004/014182 A1 | 2/2004 |
| WO | WO2004/014183 A1 | 2/2004 |
| WO | WO2004/016188 A2 | 2/2004 |
| WO | WO 2004/019801 | 3/2004 |
| WO | WO2004/026075 A1 | 4/2004 |
| WO | WO2004/026077 A1 | 4/2004 |
| WO | WO 2004/261621 | 4/2004 |
| WO | WO 2005/084486 A1 | 9/2005 |
| WO | WO2006/005624 A2 | 1/2006 |

OTHER PUBLICATIONS

Product Literature, Kraton Polymers, pp. 13-21.
Brochure, "Extrusion Lines for the Production of Monofilaments", pp. 2-12 (1989).
Plastics Extrusion Technology Handbook, Chapter 7.
Coextrusion and Dual-Extrusion Technology, pp. 168-189.
Modern Plastics Encyclopedia, 67: 138-175, 1990.
Pebax 3533 SA 00, "Base Polymer for Structural Hot Melt Adhesives".
Office Action for U.S. Appl. No. 09/979,933, dated Mar. 12, 2004; P&G Case CM1935; Solanki; filed Jun. 9, 2000.
Office Action for U.S. Appl. No. 09/979,933, dated Aug. 13, 2003; P&G Case CM1935; Solanki; filed Jun. 9, 2000.
Office Action for U.S. Appl. No. 11/071,024, dated Jun. 9, 2005; P&G Case CM1935C; Solanki; filed Mar. 2, 2005.
Office Action for U.S. Appl. No. 11/269,959, dated Jan. 10, 2006; P&G Case CM1935CC; Solanki; filed Nov. 9, 2005.
Office Action for U.S. Appl. No. 11/479,767, dated Aug. 8, 2008; P&G Case CM1935CCC; Solanki; filed Jun. 30, 2006.
Office Action for U.S. Appl. No. 11/479,767, dated Dec. 13, 2007; P&G Case CM1935CCC; Solanki; filed Jun. 30, 2006.
Office Action for U.S. Appl. No. 11/479,767, dated May 8, 2007; P&G Case CM1935CCC; Solanki; filed Jun. 30, 2006.
Office Action for U.S. Appl. No. 11/479,767, dated Dec. 7, 2006; P&G Case CM1935CCC; Solanki; filed Jun. 30, 2006.
Advisory Action for U.S. Appl. No. 08/730,286, dated Jun. 21, 1999; P&G Case Z-4168R; Masterman et al.; filed Oct. 30, 1996.
Office Action for U.S. Appl. No. 08/730,286, dated Apr. 12, 1999; P&G Case Z-4168R; Masterman et al.; filed Oct. 30, 1996.
Office Action for U.S. Appl. No. 08/730,286, dated Oct. 22, 1998; P&G Case Z-4168R; Masterman et al.; filed Oct. 30, 1996.
Office Action for U.S. Appl. No. 08/730,286, dated May 4, 1998; P&G Case Z-4168R; Masterman et al.; filed Oct. 30, 1996.
Office Action for U.S. Appl. No. 09/351,588, dated Feb. 28, 2000; P&G Case Z-4168C; Masterman et al.; filed Jul. 12, 1999.
Office Action for U.S. Appl. No. 09/660,151, dated Aug. 31, 2001; P&G Case Z-4168C2; Masterman et al.; filed Sep. 13, 2000.
Office Action for U.S. Appl. No. 09/660,151, dated Mar. 21, 2001; P&G Case Z-4168C2; Masterman et al.; filed Sep. 13, 2000.
Office Action for U.S. Appl. No. 09/660,151, dated Feb. 7, 2001; P&G Case Z-4168C2; Masterman et al.; filed Sep. 13, 2000.
Examiner's Answer for U.S. Appl. No. 10/692,916, dated Sep. 12, 2008; P&G Case Z-4168C3; Masterman et al.; filed Oct. 24, 2003.
Office Action for U.S. Appl. No. 10/692,916, dated Dec. 26, 2007; P&G Case Z-4168C3; Masterman et al.; filed Oct. 24, 2003.
Office Action for U.S. Appl. No. 10/692,916, dated Jan. 13, 2007; P&G Case Z-4168C3; Masterman et al.; filed Oct. 24, 2003.
Office Action for U.S. Appl. No. 10/692,916, dated May 19, 2006; P&G Case Z-4168C3; Masterman et al.; filed Oct. 24, 2003.
Office Action for U.S. Appl. No. 10/692,916, dated Oct. 31, 2005; P&G Case Z-4168C3; Masterman et al.; filed Oct. 24, 2003.
Office Action for U.S. Appl. No. 10/692,916, dated May 17, 2005; P&G Case Z-4168C3; Masterman et al.; filed Oct. 24, 2003.
Office Action for U.S. Appl. No. 10/692,916, dated Aug. 13, 2004; P&G Case Z-4168C3; Masterman et al.; filed Oct. 24, 2003.
Office Action for U.S. Appl. No. 10/692,916, dated May 18, 2004; P&G Case Z-4168C3; Masterman et al.; filed Oct. 24, 2003.
Examiner's Answer for U.S. Appl. No. 10/991,911, dated Sep. 11, 2008; P&G Case Z-4168C4; Masterman et al.; filed Nov. 18, 2004.
Office Action for U.S. Appl. No. 10/991,911, dated Dec. 20, 2007; P&G Case Z-4168C4; Masterman et al.; filed Nov. 18, 2004.
Office Action for U.S. Appl. No. 10/991,911, dated Nov. 17, 2007; P&G Case Z-4168C4; Masterman et al.; filed Nov. 18, 2004.
Office Action for U.S. Appl. No. 10/991,911, dated Aug. 2, 2006; P&G Case Z-4168C4; Masterman et al.; filed Nov. 18, 2004.
Examiner's Answer for U.S. Appl. No. 10/991,911, dated Jul. 10, 2006; P&G Case Z-4168C4; Masterman et al.; filed Nov. 18, 2004.
Office Action for U.S. Appl. No. 10/991,911, dated Dec. 22, 2005; P&G Case Z-4168C4; Masterman et al.; filed Nov. 18, 2004.
Office Action for U.S. Appl. No. 10/991,911, dated Jul. 12, 2005; P&G Case Z-4168C4; Masterman et al.; filed Nov. 18, 2004.
Office Action for U.S. Appl. No. 10/991,911, dated Mar. 28, 2005; P&G Case Z-4168C4; Masterman et al.; filed Nov. 18, 2004.
Office Action for U.S. Appl. No. 11/809,255, dated Jun. 27, 2008; P&G Case Z-4168C6; Roberts et al.; filed May 31, 2007.
Office Action for U.S. Appl. No. 11/809,255, dated Dec. 26, 2007; P&G Case Z-4168C6; Roberts et al.; filed May 31, 2007.
US Patent and Trademark Office Communication for U.S. Appl. No. 10/825,792, dated Feb. 22, 2008, 8 pages.
U.S. Appl. No. 11/893,470, filed Aug. 16, 2007, Chan et al.
Office Action for U.S. Appl. No. 11/893,470, dated Dec. 15, 2008; P&G Case 9215C2; Chan et al.; filed Aug. 16, 2007.
Office Action for U.S. Appl. No. 11/893,470, dated Feb. 11, 2008; P&G Case 9215C2; Chan et al.; filed Aug. 16, 2007.
Office Action for U.S. Appl. No. 10/825,792, dated May 21, 2009; P&G Case 9215; Chan et al.; filed Apr. 16, 2004.
Office Action for U.S. Appl. No. 10/825,792, dated Aug. 12, 2008; P&G Case 9215; Chan et al.; filed Apr. 16, 2004.
Office Action for U.S. Appl. No. 10/825,792, dated Jul. 6, 2007; P&G Case 9215; Chan et al.; filed Apr. 16, 2004.
Office Action for U.S. Appl. No. 10/825,792, dated Jan. 25, 2007; P&G Case 9215; Chan et al.; filed Apr. 16, 2004.
Office Action for U.S. Appl. No. 10/825,792, dated May 12, 2006; P&G Case 9215; Chan et al.; filed Apr. 16, 2004.
Office Action for U.S. Appl. No. 12/206,926 dated Jun. 1, 2009.
Office Action for U.S. Appl. No. 12/206,926 dated Jan. 11, 2010.
Office Action for U.S. Appl. No. 12/206,926 dated May 25, 2010.
Office Action for U.S. Appl. No. 12/206,926 dated Aug. 6, 2010.
Examiner's Answer for U.S. Appl. No. 11/248,087, dated Oct. 1, 2008; P&G Case Z-4168C5; Masterman et al.; filed Oct. 12, 2005.
Office Action for U.S. Appl. No. 11/248,087, dated Dec. 13, 2007; P&G Case Z-4168C5; Masterman et al.; filed Oct. 12, 2005.
Office Action for U.S. Appl. No. 11/248,087, dated Feb. 9, 2007; P&G Case Z-4168C5; Masterman et al.; filed Oct. 12, 2005.
Office Action for U.S. Appl. No. 11/248,087, dated Jun. 15, 2006; P&G Case Z-4168C5; Masterman et al.; filed Oct. 12, 2005.
PCT International Search Report dated Mar. 17, 1997.
"Standard Test Methods for Flexural Properties of Unreinforced and Reinforced Plastics and Electrical Insulating Materials [Metric]", American Society for Testing Designation: D790M-93 Metric, pp. 1-9, Undated.
"Standard Terminology Relating to Plastics", American Society for Testing Materials, Designation: D883-00, pp. 1-15, Undated.

(56) References Cited

OTHER PUBLICATIONS

"Santroprene Rubber Physical Properties Guide, Tensile Properties, Dynamic Mechanical Properties, Tension and Compression Set, Fatigue Resistance," Advanced Elastomer Systems, pp. 2-19, Undated.

Hendricks et al., "Rubber-Related Polymers I. Thermoplastic Elastomers", Rubber Technology, pp. 515-533, undated.

"Plastics Determination of Flexural Properties," British Standard, BX EN ISO 178:2003, Apr. 9, 2003.

European equivalent EP 0918477 Opposition Documents.

AU 148045 S Industrial Design Application (The Procter & Gamble Company), Jun. 4, 2002, [online], [retried on May 29, 2006] Retrieved from the Australian Government IP Australia Design Database using the Internet URL: http:www.ipaustralia.gov.au.

Office Action for U.S. Appl. No. 11/317,842 dated Jul. 28, 2006; P&G Case CM1137CCC; Cann; filed Dec. 23, 2005.

Office Action for U.S. Appl. No. 11/317,842 dated Mar. 16, 2007; P&G Case CM1137CCC; Cann; filed Dec. 23, 2005.

Office Action for U.S. Appl. No. 11/317,842 dated Dec. 27, 2007; P&G Case CM1137CCC; Cann; filed Dec. 23,. 2005.

Office Action for U.S. Appl. No. 11/317,842 dated Jul. 15, 2008; P&G Case CM1137CCC; Cann; filed Dec. 23, 2005.

Office Action for U.S. Appl. No. 11/317,842 dated Jan. 26, 2009; P&G Case CM1137CCC; Cann; filed Dec. 23, 2005.

Office Action for U.S. Appl. No. 11/317,842 dated Jul. 8, 2009; P&G Case CM1137CCC; Cann; filed Dec. 23, 2005.

Office Action for U.S. Appl. No. 11/317,842 dated Oct. 13, 2009; P&G Case CM1137CCC; Cann; filed Dec. 23, 2005.

Office Action for U.S. Appl. No. 11/317,842 dated Oct. 6, 2010; P&G Case CM1137CCC; Cann; filed Dec. 23, 2005.

Office Action for U.S. Appl. No. 11/317,842 dated Mar. 25, 2011; P&G Case CM1137CCC; Cann; filed Dec. 23, 2005.

Office Action for U.S. Appl. No. 10/991,911, dated Dec. 14, 2010; P&G Case Z-4168C4; Masterman et al.; filed Nov. 18, 2004.

Office Action for U.S. Appl. No. 12/722,430, dated Sep. 24, 2010; P&G Case CM1935CCCC; Solanki; filed Mar. 11, 2010.

* cited by examiner

ELECTRIC TOOTHBRUSHES

CROSS REFERENCE TO RELATED APPLICATION

The application is a continuation of U.S. patent application Ser. No. 10/825,792, filed on Apr. 16, 2004 now abandoned, which claims the benefit of U.S. Provisional Application No. 60/464,787, filed Apr. 23, 2003, the substance of which is incorporated by reference in their entirety herein.

FIELD OF THE INVENTION

The present invention relates to the field of toothbrushes, and more particularly, the invention relates to the field of electrically powered toothbrushes.

BACKGROUND OF THE INVENTION

Most known electric toothbrushes utilize a single bristle carrier that is powered or otherwise driven by an electric motor incorporated in the toothbrush. The bristle carriers in these toothbrushes generally undergo rotary motion. Although satisfactory in certain respects, a need still exists for an improved powered toothbrush design.

Numerous attempts have been made to improve the design, efficiency, cleaning efficacy, simplicity, and/or commercial viability of electric toothbrushes. One approach has been the provision of multiple powered bristle carriers. Most artisans have grouped multiple sets of bristles along an end of a brush and incorporated a drive mechanism for simultaneously rotating each of the bristle sets, together. Exemplary designs include those disclosed in U.S. Pat. Nos. 3,242,516; 4,156,620; 4,845,795; 5,088,145; 5,020,179; 4,827,550; and 4,545,087.

A related strategy is to group sets of bristles on multiple rotating bristle carriers, as disclosed in U.S. Pat. Nos. 2,140,307 and 5,170,525. Rather than rotating each individual bristle set about its center, i.e. the approach adopted in the previously noted patents, the designs described in the '307 and '525 patents rotate multiple groups of bristle sets about the center of a bristle carrier. Specifically, multiple groups of bristle sets are disposed on a circular bristle carrier and that bristle carrier, typically one of several, is rotated about its own axis.

U.S. Pat. No. 5,070,567 describes a design combining the two previously noted strategies. A rotating bristle carrier is provided along with multiple individually rotatable bristle sets. Although this design likely provides many of the advantages associated with each of its predecessors, the cleaning efficacy of spinning bristle sets, alone, is somewhat limited.

Yet another design is disclosed in U.S. Pat. No. 5,617,603. The '603 patent describes an assembly of "staggered swing" brushes. Apparently, the two bristle carriers move along a complex path within the plane of the toothbrush.

Although dual bristle carriers that undergo various combinations of movement have been disclosed in the prior art, there remains a need to provide an electric toothbrush with a plurality of bristle carriers in which at least one carrier undergoes a reciprocating or pivotal type of motion. Additionally, there is a need to provide an electric toothbrush with multiple bristle carriers in which at least one of the carriers reciprocates while another component of the brush undergoes a particular type of motion that assists in the brushing operations.

SUMMARY OF THE INVENTION

An electric toothbrush is provided. The electric toothbrush has an elongated body including a handle, a head, and a neck extending between the handle and the head. A plurality of bristle carriers are disposed on the head and each of the bristle carriers include a collection of bristle tufts. An electric motor is operatively connected to a shaft, both of which are disposed in the body of the toothbrush. Upon operation of the electric motor, the shaft moves in a reciprocating motion. The shaft is operatively connected to at least one of the bristle carriers to move that carrier and associated carriers.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which.

DETAILED DESCRIPTION OF THE PREFERRED EMBODIMENTS

Before describing the various preferred embodiments, it is instructive to define the various types of motions that the movable bristles of the various toothbrushes may undergo. As used herein, the term "angular motion" refers to any angular displacement. "Linear motion" is movement along a straight or substantially straight, line or direction. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion is referred to as rotary motion, although features herein may be described as "rotatably mounted" which is intended to merely mean that angular motion, whether periodic or constant, is possible. Periodic angular motion is referred to as oscillating motion. Curvilinear motions can also be either constant (i.e., unidirectional) or periodic (i.e., reverses direction). Periodic linear motion is referred to as "reciprocation". "Orbital motion" is a type of angular motion about an axis that is distinct from and is some distance apart from the center of the moving component, e.g. a shaft. This distance is referred to herein as the extent of offset of the orbital motion. Orbital motion may be either constant angular motion or periodic angular motion.

Figure 1:
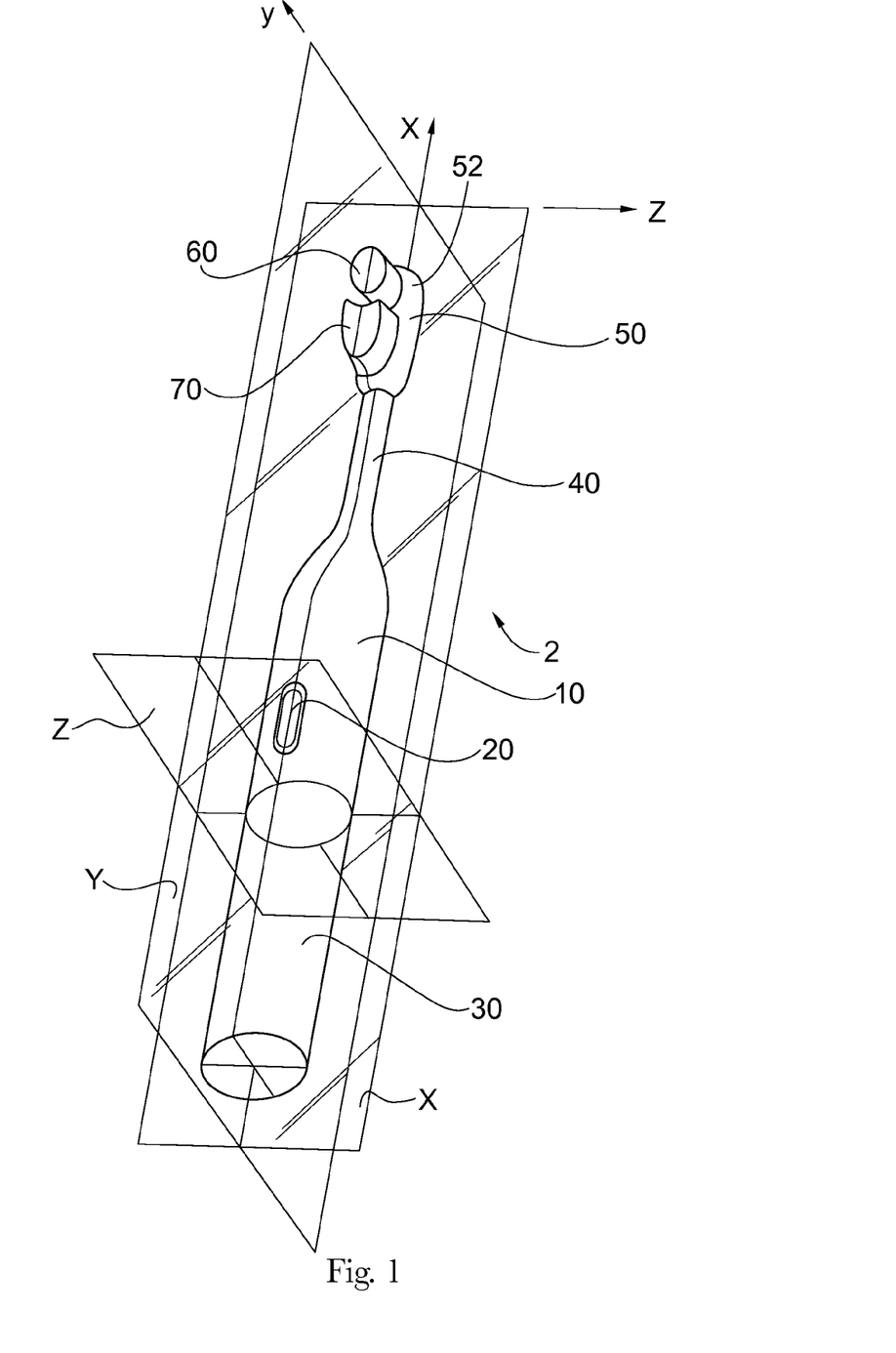
FIG. 1 is a perspective view of a preferred embodiment toothbrush in accordance with the present invention illustrating various planes and their orientation with respect to the toothbrush.

The above-described motions can occur along one or more axes of a bristle carrier, a toothbrush, a toothbrush head, etc. Accordingly, motion is described herein as being either one, two, or three dimensional motion depending upon the number of axial coordinates required to describe the position of a bristle carrier during its movement. The axes, X, Y, and Z, are shown in FIG. 1. One dimensional motion is motion that can be described by a single coordinate (e.g., X, Y, or Z coordinates). Typically, only linear motion can be one dimensional. For example, periodic linear motion substantially along only the Y axis is one dimensional motion (referred to herein as a "pulsing motion" or an "up and down motion"). Two dimensional motion is movement by a bristle carrier that requires two coordinates (e.g., X and Y coordinates) to describe the path of travel of the bristle carrier. Angular motion that occurs in a single plane is two dimensional motion since a point on a bristle carrier would need two coordinates to describe the path of travel. Three dimensional motion is movement by a bristle carrier that requires three coordinates (e.g., X, Y, and Z coordinates) to describe the path of travel of the bristle carrier. An example of three dimensional motion is movement by a bristle carrier in the path of a helix.

Since most of the bristle carrier motions described herein can be modified by adjusting various structural features, the description of a motion herein shall be automatically understood to accommodate these variations. For example, a motion that is described as oscillating about an axis can also include components of other motions (e.g., a reciprocating linear motion), especially where it is noted that modifications can be made to provide this second component of motion. Motions that are intended to exclude such modifications shall be described herein with the modifier "primarily" (e.g., "primarily oscillating" or "primarily reciprocating") and are intended to exclude significant other types motion, but not other motions that might be incidental from manufacturing tolerances or variabilities or where it is difficult to completely eliminate another type of motion completely from the bristle carrier, as is sometimes the case. All motions described herein may be restricted to primarily the motion described if desired.

FIG. 1 is a perspective view of a preferred embodiment toothbrush 2 in accordance with the present invention. The toothbrush 2 comprises an elongated body 10 having a handle 30, a head 50, and a neck 40 extending between the handle 30 and the head 50. A switch 20 is provided or made accessible along the outer region of the body 10. As will be appreciated, the switch 20 actuates an electrical motor contained within the body 10 of toothbrush 2. The motor (not shown) and a drive mechanism as described herein (not shown) drive one or more bristle carriers disposed near a distal end of the toothbrush. Specifically, the toothbrush 2 further includes a first bristle carrier 60 located adjacent a distal-most first end 52 and a second bristle carrier 70. As described in greater detail herein, upon activation of the drive mechanism, the first and second bristle carriers undergo a particular combination of motions. The motions are best described in terms of the axes X, Y, and Z.

The X axis is generally referred to herein as the longitudinal axis and generally extends along a longitudinal or lengthwise dimension (as seen from the top planar view of the toothbrush) of the toothbrush head or the bristle carrier. For example, a longitudinal axis is an axis passing through the longest dimension of the toothbrush head. The Y axis is transverse, orthogonal or perpendicular to the X axis and generally bisects the toothbrush head into its left and right halves. The Z axis is transverse, orthogonal or perpendicular to the X and Y axes. It will be appreciated that axis orientations need not be exactly orthogonal or perpendicular to another axis and that some deviation from 90 degrees between the axes, particularly when these axes are used to describe a direction of motion. It should be understood that any axis orientation herein can be modified by the terms "generally" or "substantially" (e.g., "generally transverse" or "substantially transverse"). The word "substantially" implies some angular deviation, but not as much angular deviation from 90 degrees as the word "generally". No modifier indicates slight to no deviation from 90 degrees. Thus, a motion that is described as occurring along a first axis transverse to a second axis implies that the motion occurs at a 90 degree angle to the second axis with some slight deviation permitted (e.g., from manufacturing tolerances, etc.). If the motion is generally transverse or substantially transverse, a greater deviation from 90 degrees is contemplated. All the axes described herein can intersect another axis either generally or substantially transverse to said other axis.

Plane X contains the X axis and is generally referred to herein as the plane of the toothbrush or the plane of the toothbrush head. This plane generally extends along the longitudinal dimension of the toothbrush. The Y plane contains the Y axis and extends through the toothbrush and is perpendicular to the X plane. The Y plane either bisects the toothbrush or is parallel to a plane that does. The Z plane is perpendicular to both the X plane and the Y plane and contains the Z axis.

Furthermore, it is useful to address the terminology used in describing the preferred embodiment toothbrushes, bristle carriers, and the various drive mechanisms. As used herein, the term "forward" refers to the direction from the handle to the head while the term "rearward" refers to the direction from the head to the handle. A longitudinal direction is a direction that generally corresponds to a longitudinal or X axis but which may not lie in the same plane as the axis. For example, the longitudinal axes of a shaft and a bristle carrier may not extend in the same plane but generally extend in the same direction from a top planar view. Similarly, a neck and head that are angled with respect to each other may not have longitudinal axes that extend in the same plane, but do have axes that extend in the same general longitudinal direction from a top planar view. Many of the preferred embodiment electric toothbrushes typically have an elongated head with a longitudinal axis passing through the longest dimension thereof. This axis typically extends in the same general direction as the longitudinal axes of the toothbrush neck and/or shaft. This axis is generally referred to as the longitudinal axis of the toothbrush. By the phrase "same general direction," some angular deviation is contemplated between the axes.

Generally, the preferred embodiment toothbrushes according to the present invention comprise an elongated hollow body containing an electrically powered motor and drive mechanism that is used to drive one, two, three or more moveable bristle carriers. The elongated hollow body also includes an interior chamber or cavity for containing one or more batteries for powering the motor. And, one or more switches are provided along the outer region of the body for activating the motor and drive mechanism. As will be appreciated, a removable end cap is provided to enclose the interior chamber and provide a seal against external agents for the components inside the toothbrush body. As described in detail herein, the preferred embodiment toothbrushes comprise one, two, three or more movable bristle carriers. Each of the bristle carriers undergoes particular types of motion and the resulting combinations of movements provide unique cleaning efficacy.

Furthermore, it is useful to define the terms "fixed" or "static" bristles, and the term "movable" bristles. The terms fixed or static bristles refer to bristles that are secured or affixed to the brush head or body of the toothbrush or other component thereof so that the bristles, and specifically, the base of the bristles, do not move with regard to the longitudinal axis of the toothbrush. Restated, fixed or static bristles refer to bristles that are affixed to the toothbrush such that their base or point of attachment does not move with respect to the toothbrush. It is recognized that the tips or regions distal from the base of a bristle or group of bristles may move as a result of flexing of the bristle. However, the base of a stationary, static, or fixed bristle does not move with respect to the brush. The term movable bristle refers to a bristle in which the base of the bristle moves with respect to the toothbrush, and particularly with respect to the longitudinal axis of the brush. Generally, this configuration is accomplished by affixing or supporting the base of the bristle to a mounting component, i.e. a bristle carrier or holder, that is movable with respect to the brush. Restated, a movable bristle is a bristle that is movable with respect to the longitudinal axis of the brush.

Figure 2:
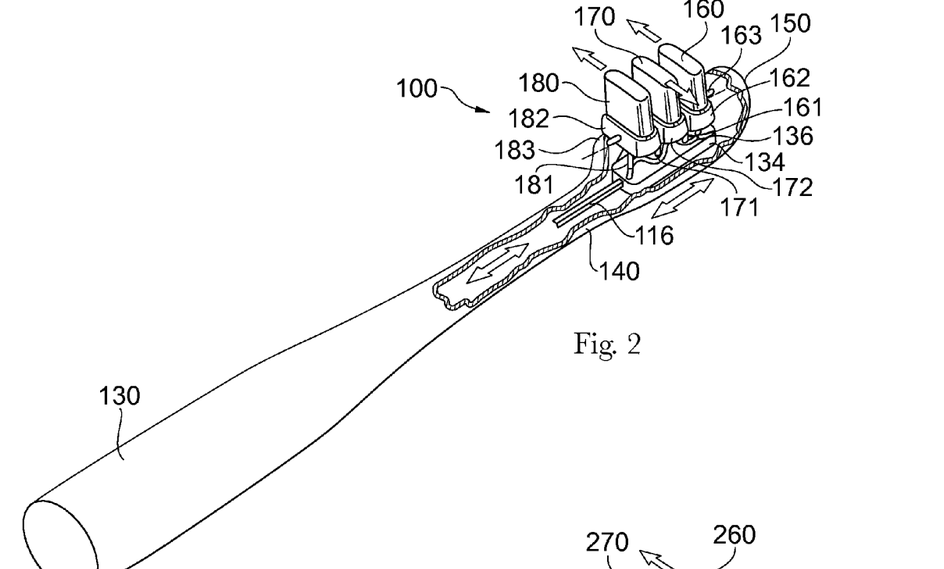
FIG. 2 is a perspective view of another preferred embodiment toothbrush in accordance with the present invention.

FIG. 2 is a partial perspective view of a preferred embodiment toothbrush 100 in accordance with the present invention. The preferred embodiment toothbrush 100 includes a body 130, a brush head 150, and a neck 140 extending between the body and the head. The toothbrush 100 further includes a bristle carrier assembly that features a plurality of bristle carriers as follows. This preferred assembly includes a first bristle carrier 160, a second bristle carrier 170, and a third bristle carrier 180. The first bristle carrier 160 includes a base 162. The second bristle carrier 170 includes a base 172. And, the third bristle carrier 180 includes a base 182. Preferably, the first, second, and third bristle carriers, i.e. 160, 170, and 180 are pivotable (when incorporated in a toothbrush head) about an axis extending through one or more pivot members such as pivot members 183 and 163. Each of the bases 162, 172, and 182 contain a camming member 161, 171, and 181, each of which is received within a camming slot 136 defined within a cam member 134. Each of the camming members 161, 171, and 181 preferably extends downward from a respective base, as shown in FIG. 2. The cam member 134 is retained within the interior of the toothbrush head and is engaged with a drive shaft 116. As can be seen, the drive shaft 116 preferably undergoes a reciprocating-type motion. Upon reciprocal movement of the drive shaft 116; reciprocal movement, however transverse to the movement of the drive shaft 116, or periodic curvilinear movement is imparted to each of the bristle carriers 160, 170, and 180. The specific type of motion imparted to each of the bristle carriers depends upon the configuration and engagement between the camming members and the camming slot.

Figure 3:
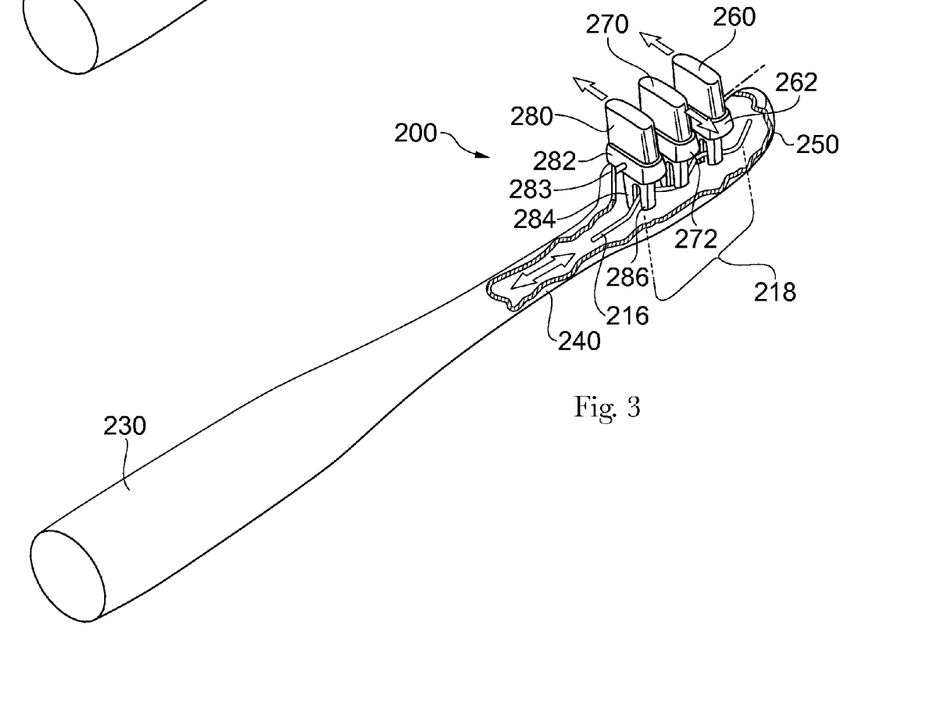
FIG. 3 is a perspective view of another preferred embodiment toothbrush in accordance with the present invention.

FIG. 3 is a perspective view of another preferred embodiment toothbrush 200 in accordance with the present invention. The preferred embodiment toothbrush 200 includes a body 230, a brush head 250, and a neck 240 extending between the body and the head. The toothbrush 200 further includes a bristle carrier assembly that features a plurality of bristle carriers as follows. FIG. 3 illustrates the assembly as comprising a first bristle carrier 260, a second bristle carrier 270, and a third bristle carrier 280. The first bristle carrier 260 includes a base 262. The second bristle carrier 270 includes a base 272. The third bristle carrier 280 includes a base 282. Preferably, each of the bases, i.e., 262, 272, and 282, provide a collar which defines an engagement slot or aperture. For example, as shown in FIG. 3, the third bristle carrier 280 includes a collar 284 that defines an engagement slot or aperture 286. Each of the slots or apertures of a respective collar is received along a cam region 218 of a drive shaft 216. Preferably, the drive shaft 216 undergoes reciprocating motion such that lateral motion or other motion is imparted to each of the bristle carriers 260, 270, and 280. As previously explained with regard to FIG. 2, one or more of the bristle carriers 260, 270, 280 may include a pivot member such as member 283 in FIG. 3. Depending upon their configuration and engagement with a retaining component of a toothbrush head within which the bristle carrier assembly is incorporated, the pivot members generally serve to cause the bristle carriers to undergo a pivotal motion about the axis of the pivot members.

Figure 4:
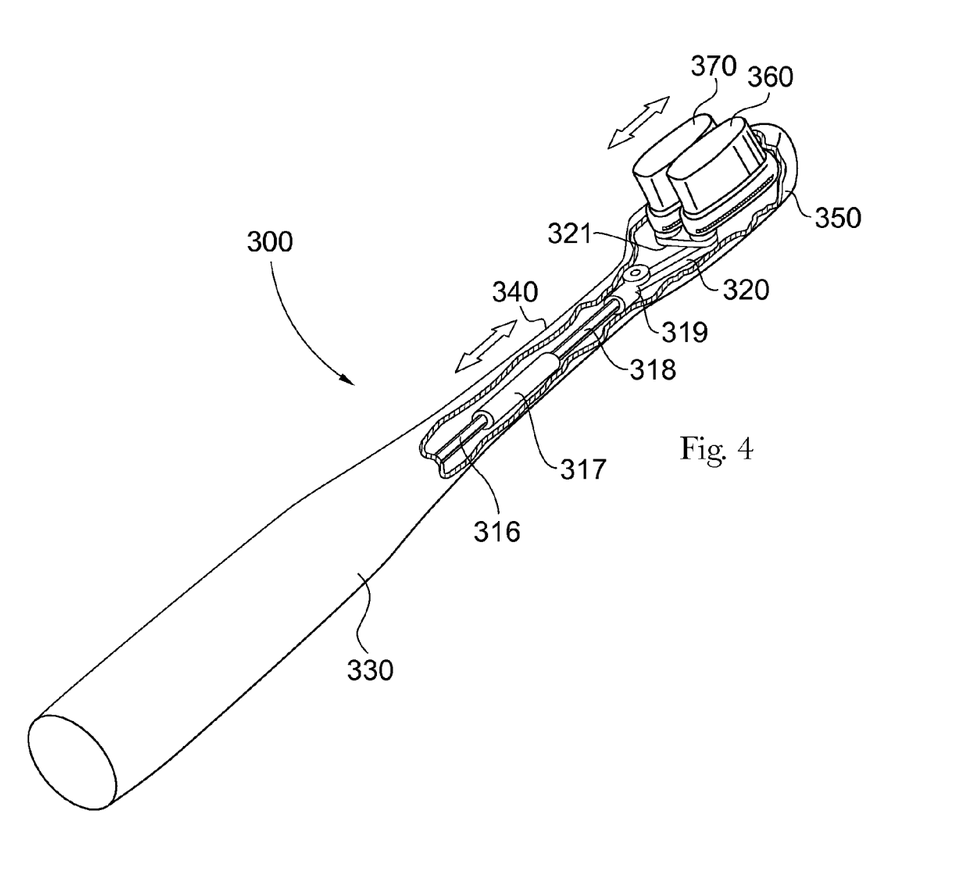
FIG. 4 is a perspective view of another preferred embodiment toothbrush in accordance with the present invention.

FIG. 4 is a perspective view of another preferred embodiment toothbrush 300 in accordance with the present invention. This preferred embodiment toothbrush 300 comprises a body 330, a head 350, and a neck 340 extending between the body 330 and the head 350. Disposed on the brush head 350 are a plurality of movable bristle carriers which in FIG. 4 as shown, include a first bristle carrier 360 and a second bristle carrier 370. Each of the bristle carriers 360 and 370 undergo a reciprocating motion as shown upon activation of the brush. Specifically, linear reciprocating motion of a drive shaft 316, such as from a drive mechanism (not shown) disposed in the body 330 is imparted to a second drive shaft 318 via linkage 317. Movement of drive shaft 318 is further transmitted to a hinged component 319 and to a linking arm 320 extending between the hinged component 319 and one or both of the bristle carriers 360 and 370.

In a most preferred aspect, a rocking arm 321 is utilized that extends between the first and second bristle carriers 360 and 370. Most preferably, the rocking arm 321 is hinged about its center to a stationary member within the interior of the brush head 350 such that the arm 321 may move or pivot about that member. An end of the linking arm 320 is engaged to an end of the rocking arm 321 such that reciprocation of the linking arm 320 causes pivoting of the arm 321 about its center. As shown in FIG. 4, since each bristle carrier 360 and 370 is engaged to an opposite end of the rocking arm 321, pivoting of the arm 321 causes reciprocation of the carriers 360 and 370. The reciprocation of each carrier 360 and 370 is out of phase with the other. Thus, when the carrier 360 moves in a forward direction, the carrier 370 moves in a rearward direction, and vice versa.

Figure 5:
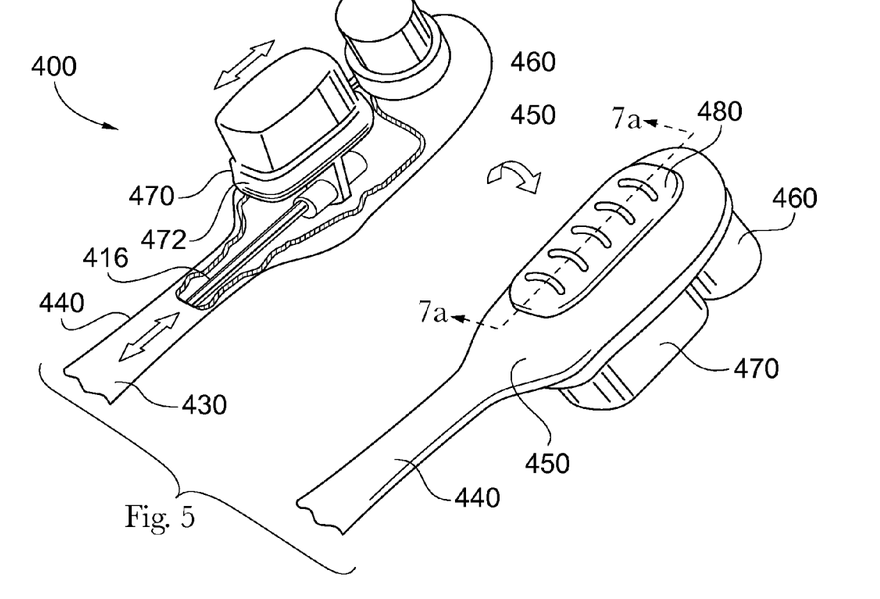
FIG. 5 is a perspective view of the front and rear of a brush head of another preferred embodiment toothbrush in accordance with the present invention.
Figure 6:
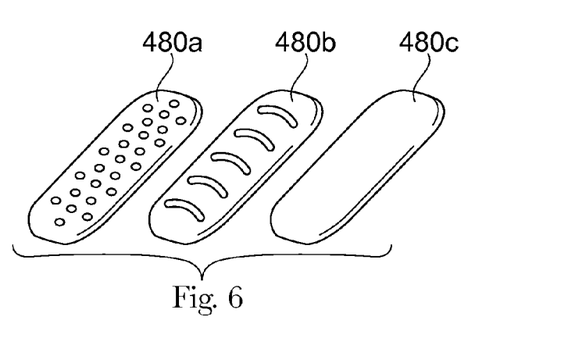
FIG. 6 is a detailed view of several preferred massaging elements utilized by the preferred embodiment toothbrush depicted in FIG. 5.
Figure 7A:
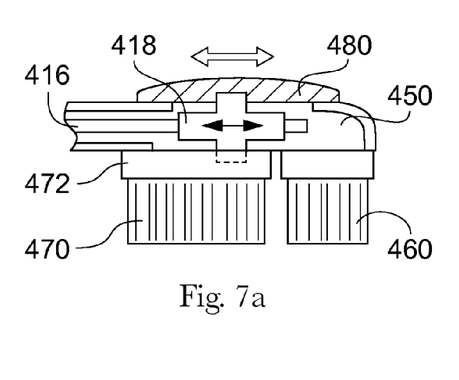
FIG. 7a is a detailed cross sectional view of the brush head of the preferred embodiment toothbrush shown in FIG. 5.
Figure 7B:
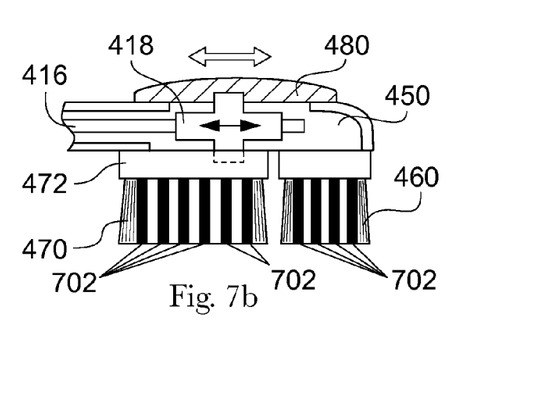
FIG. 7b is a cross sectional view of a brush head in accordance with another embodiment.

FIGS. 5, 6, and 7 illustrate yet another preferred embodiment toothbrush 400 in accordance with the present invention. The preferred embodiment toothbrush 400 includes a body 430, a head 450, and a neck 440 extending between the body 430 and the brush head 450. Disposed on the brush head 450 are a plurality of movable bristle carriers such as a first bristle carrier 460 and a second bristle carrier 470. A drive shaft 416 extends within the neck 440 and the body 430 and imparts motion to one or both of the bristle carriers 460 and 470 from a drive mechanism (not shown). Preferably, upon operation of the toothbrush 400, the drive shaft 416 reciprocates as shown in FIG. 5. The distal end of the drive shaft 416 is engaged with a base 472 of the second bristle carrier 470. As will be appreciated, the first bristle carrier 460 may be directly powered from the drive shaft 416 or indirectly powered, such as via the second bristle carrier 470.

The preferred embodiment toothbrush 400 of FIGS. 5, 6, and 7 features a massaging plate 480 movably disposed along a rear face of the brush head 450. Upon operation of the toothbrush 400, the massaging plate 480 is reciprocated generally along the longitudinal axis of the toothbrush 400. The massaging plate is preferably formed from an elastomeric material, or other relatively soft pliable material. The outer surface of the massaging plate 480 may be formed so as to provide one or more outwardly extending ridges, protrusions, or other members that serve to provide specific massaging characteristics. FIG. 6 illustrates various alternative versions of the massaging plate 480. A plate 480a may be provided that has a plurality of raised protrusions or other projections extending from its outer surface. A plate 480b may be used that features a plurality of outwardly extending ridges. And, a plate 480c may be used that features a relatively smooth outer surface, free of any raised or outwardly extending projections.

FIG. 7a is a partial sectional elevational view of the brush head 450 of the toothbrush depicted in FIG. 5 taken along line VII-VII. FIG. 7a illustrates a linking component 418 that engages the distal end of the drive shaft 416 to the bristle carrier 470 and to the massaging plate 480. Upon reciprocating motion of the drive shaft 416, both the bristle carrier 470 and the massaging plate 480 are moved in similar fashion.

Another embodiment of a toothbrush is shown in FIG. 7b. Disposed on the brush head 450 are a plurality of movable bristle carriers such as a first bristle carrier 460 and a second bristle carrier 470. The bristle carriers include massaging tips 702. The massaging tips 702 massage the gums while the user brushes his or her teeth. The massaging tips 702 can be made from a rubber, soft plastic or similar material. The massaging tips 702 extend essentially perpendicularly from the head 450 as measured along a longitudinal axis. In one embodiment, the massaging tips 702 are located around the perimeter of the head 450, however it is to be understood that the massaging tips can be located anywhere among the bristle carriers. The length of the massaging tips 702 is approximately the same length as the bristle carriers 460 and 470. The massaging tips 702 may extend slightly above, slightly below or to the same height as the bristle carriers 460 and 470.

Figure 8:
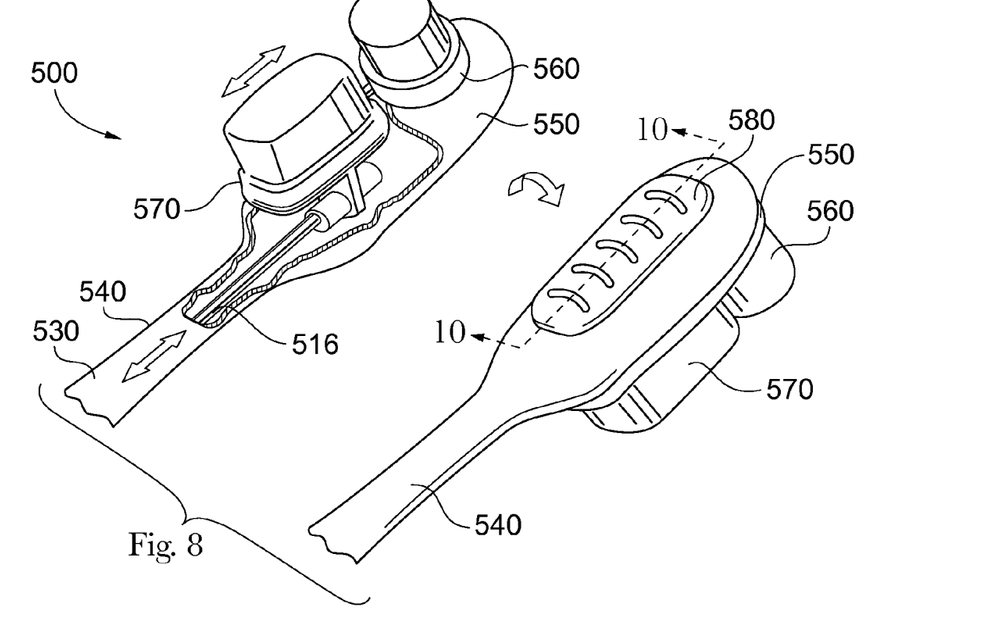
FIG. 8 is a detailed view of the front and rear of a brush head of another preferred embodiment toothbrush in accordance with the present invention.
Figure 9:
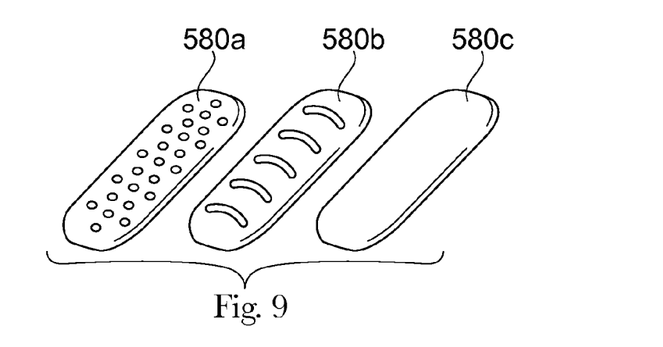
FIG. 9 is a detailed view of several preferred massaging elements utilized by the preferred embodiment toothbrush depicted in FIG. 8.
Figure 10:
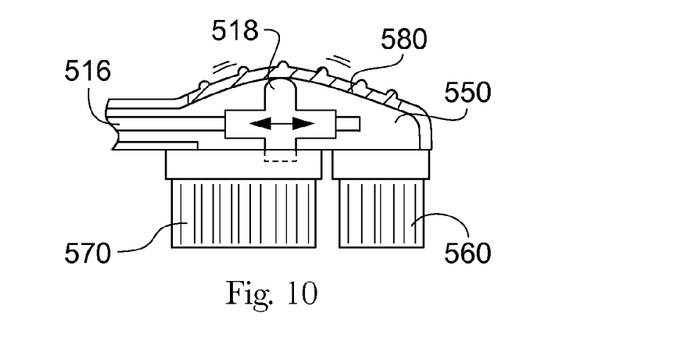
FIG. 10 is a detailed cross sectional view of the brush head of the preferred embodiment toothbrush shown in FIG. 8.

FIGS. 8, 9, and 10 illustrate yet another preferred embodiment toothbrush 500 in accordance with the present invention. The toothbrush 500 includes a body 530, a brush head 550, and a neck 540 extending between the body 530 and the brush head 550. A first bristle carrier 560 is disposed on the brush head 550. And, a second bristle carrier 570 is disposed on the brush head 550. A drive shaft 516 extends within the neck 540 and upon activation of the brush, imparts motion to one or both of the bristle carriers 560 and 570.

The toothbrush 500 provides a massaging plate 580 similar to the toothbrush 400 previously described. However, the massaging plate 580 of the toothbrush 500 does not reciprocate as does the massaging plate 480 of the toothbrush 400. This is described in greater detail herein. The massaging plate 580 is preferably formed from an elastomeric or other suitable material. The plate 580 is preferably disposed along a rearward face of the toothbrush head 550 and secured thereto. The plate 580 may be provided with a variety of different surface configurations. FIG. 9 depicts a massaging plate 580a having a plurality of outwardly extending raised regions; plate 580b having a plurality of raised ridges; and plate 580c having a smooth outer surface.

FIG. 10 is a partial sectional elevational view of the brush head 550 of the toothbrush 500 taken along line X-X in FIG. 8. A linking component 518 is provided that engages the distal end of the drive shaft 516 to the bristle carrier 570. The linking component 518 is provided with an outwardly extending bulb or region that contacts the underside of the massaging plate 580. As will be appreciated, since the plate 580 is formed from a material that is flexible and pliable, motion is imparted to the outer surface of the plate 580 as the linking component 518 is displaced along the underside of the plate 580. This configuration results in the outer surface of the massaging plate 580 exhibiting a pulsing motion and essentially vibrate upon operation of the toothbrush 500.

It will be appreciated that in all of the embodiments of the present invention, one or more groups of static bristles or other cleaning members may be provided in conjunction with the moving bristles. It may, in many instances, be preferred to provide a collection of static bristles on the toothbrush head. For example, static bristles may be disposed in a gap between bristle carriers or may completely encircle the bristle carriers. Static bristles may also be disposed at the distal-most end of the head and/or at the rearward-most portion of the head and/or adjacent the sides of the toothbrush head. Further examples of static bristles that may be used with the present invention are described in U.S. patent application Ser. No. 10/274,40 and U.S. Pat. No. 6,360,395. Moving or static elastomeric bristles, formed for example from a thermoplastic elastomer or rubber, can also be provided on the moving bristle carriers or the toothbrush head. An example of one arrangement is described in U.S. Pat. No. 6,371,294.

While brush head embodiments of the present invention have been illustrated for simplicity with tufts of bristles that extend in a direction substantially perpendicular to the longitudinal axis of the head from which they extend, it is contemplated that the static and/or movable bristles might be arranged differently to compliment or further enhance the static bristles or the motion of the movable bristles. Some or all of the bristles might extend in a direction that forms an acute angle with a top surface of a bristle holder and may extend in a forward or rearward direction. In another embodiment, some of the bristles might extend outwardly away from the head, in another direction, again forming an acute angle with respect to the top surface of the bristle holder. Examples of other suitable bristle arrangements are described in U.S. Pat. Nos. Des. 330,286, Des. 434,563; 6,006,394; 4,081,876; 5,046,213; 5,335,389; 5,392,483; 5,446,940; 4,894,880; and International Publication No. WO99/23910.

The toothbrushes of the present invention may be formed from a wide array of polymers. In the following description of the preferred polymer materials for use herein, the abbreviations that are commonly used by those of skill in the art to refer to certain polymers appear in parentheses following the full names of the polymers. The polymer is preferably polypropylene ("PP"), or may be selected from the group consisting of other commercially available materials, such as polystyrene ("PS"), polyethylene ("PE"), acrylonitrile-styrene copolymer ("SAN"), and cellulose acetate propionate ("CAP"). These materials may be blended with one or more additional polymers including a thermoplastic elastomer ("TPE"), a thermoplastic olefin ("TPO"), a soft thermoplastic polyolefin (e.g., polybutylene), or may be selected from other elastomeric materials, such as etheylene-vinylacetate copolymer ("EVA"), and ethylene propylene rubber ("EPR"). Examples of suitable thermoplastic elastomers herein include styrene-ethylene-butadiene-styrene ("SEBS"), styrene-butadiene-styrene ("SBS"), and styrene-isoprene-styrene ("SIS"). Examples of suitable thermoplastic olefins herein include polybutylene ("PB"), and polyethylene ("PE"). Techniques known to those of skill in the art, such as injection molding, can be used to manufacture the toothbrush of the present invention.

The present invention has been described with reference to particular preferred embodiments. Modifications and alterations may be made to these embodiments within the scope of the present invention. For example, certain combinations of bristle carriers have been described herein. It will be appreciated that the bristle carriers can be rearranged and the bristle carrier of one embodiment substituted for that of another. Further, while some bristle carriers may have a slot that engages a pin on the toothbrush head to guide the movement of the bristle carrier, it will be appreciated that these features can be reversed so that the pin is disposed on the bristle carrier and the slot is disposed on the head, and further that other structures known in the art can be used to guide the motion of any of the bristle carriers described herein. It is intended that all such modifications and alterations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush having a body, a brush head, and a neck extending between the body and the brush head, the brush head having a forward face and a rear face, the toothbrush further comprising:
    a massaging element disposed on the rear face of the brush head;
    a plurality of bristles extending from the forward face, wherein a portion of the bristles are static and a portion of the bristles are movable when in use;
    a drive mechanism for imparting vibration to the massaging element; and wherein at least a portion of the massaging element is coplanar with the rear face.

2. The toothbrush of claim 1, wherein the massaging element is made from an elastomeric material.

3. The toothbrush of claim 1, wherein the massaging element comprises a plurality of outwardly extending ridges.

4. The toothbrush of claim 3, wherein the plurality of outwardly extending ridges are generally perpendicular to a longitudinal axis of the toothbrush.

5. The toothbrush of claim 1, wherein the massaging element comprises a plurality of outwardly extending protrusions.

6. The toothbrush of claim 1, wherein the massaging element comprises a plurality of outwardly extending members which are capable of providing massaging.

7. The toothbrush of claim 1, further comprising elastomeric bristles disposed adjacent to sides of the brush head.

8. The toothbrush of claim 7, wherein the elastomeric bristles have a height which is less than the height of the plurality of bristles.

9. The toothbrush of claim 1, wherein the toothbrush further comprises an outwardly extending region which contact an underside of the massaging element.

10. The toothbrush of claim 1, wherein a portion of the plurality of bristles extend in a direction which forms an acute angle with the front face of the brush head.

11. The toothbrush of claim 10, wherein the portion of the plurality of bristles extend in a forward direction.

12. The toothbrush of claim 10, wherein the portion of the plurality of bristles extend in a rearward direction.

13. The toothbrush of claim 12, further comprising another portion of the plurality of bristles which extend in the rearward direction thereby forming an acute angle with respect to the front face of the brush head.

14. An electric toothbrush having a body, a brush head, and a neck extending between the body and the brush head, the brush head having a forward face and a rear face, the toothbrush further comprising:
    a massaging element disposed on the rear face of the brush head, wherein the massaging element comprises a plurality of outwardly extending protrusions; and wherein at least a portion of the massaging element is coplanar with the rear face;
    a plurality of bristles extending from the forward face, wherein a portion of the bristles are static and a portion of the bristles are movable when in use;
    a drive mechanism for imparting vibration to the massaging element; and
    a plurality of elastomeric bristles extending from the forward face, wherein the plurality of elastomeric bristles are disposed adjacent to sides of the brush head.

15. The toothbrush of claim 14, wherein the toothbrush further comprises an outwardly extending portion which contacts the underside of the massaging element.

16. The toothbrush of claim 14, wherein the elastomeric bristles have a height which is less than the height of the plurality of bristles.

17. The toothbrush of claim 14, wherein the elastomeric bristles and the massaging element are made from a thermoplastic elastomer.

18. The toothbrush of claim 14, wherein a portion of the plurality of bristles extend in a direction which forms an acute angle with the front face of the brush head.

19. The toothbrush of claim 18, wherein the portion of the plurality of bristles extend in a forward direction.

20. The toothbrush of claim 18, wherein the portion of the plurality of bristles extend in a rearward direction.

21. The toothbrush of claim 19, further comprising another portion of the plurality of bristles which extend in the rearward direction thereby forming an acute angle with respect to the front face of the brush head.

* * * * *